US005744647A

United States Patent [19]
Hsu et al.

[11] Patent Number: 5,744,647
[45] Date of Patent: Apr. 28, 1998

[54] PROCESS FOR THE PREPARATION OF 3-(METHYLTHIO) PROPANAL

[75] Inventors: Yung C. Hsu, Chesterfield; Dennis A. Ruest, Manchester, both of Mo.

[73] Assignee: Novus International, Inc., St. Louis, Mo.

[21] Appl. No.: 679,701

[22] Filed: Jul. 11, 1996

Related U.S. Application Data

[63] Continuation of Ser. No. 557,699, Nov. 13, 1995, which is a continuation of Ser. No. 273,216, Jul. 11, 1994, abandoned, which is a continuation-in-part of Ser. No. 73,763, Jun. 8, 1993, Pat. No. 5,352,837.

[51] Int. Cl.$^6$ .................................................. C07C 323/50
[52] U.S. Cl. ........................... 568/41; 568/38; 568/39; 568/42
[58] Field of Search ............................... 568/38, 41, 39, 568/42

[56] References Cited

U.S. PATENT DOCUMENTS

| | | | |
|---|---|---|---|
| 2,542,768 | 2/1951 | Gresham et al. | 260/465.6 |
| 2,564,105 | 8/1951 | Gresham et al. | 260/465.6 |
| 2,626,282 | 1/1953 | Cunningham et al. | 260/601 |
| 2,676,190 | 4/1954 | Bernard et al. | 260/601 |
| 2,776,996 | 1/1957 | Hunt et al. | 260/601 |
| 3,438,868 | 4/1969 | Sawaki et al. | 203/8 |
| 3,529,940 | 9/1970 | Shima et al. | 23/288 |
| 3,574,766 | 4/1971 | Meyer et al. | 260/601 |
| 3,833,651 | 9/1974 | Ouchi et al. | 260/534 S |
| 3,878,057 | 4/1975 | Mannsfeld | 203/35 |
| 4,048,232 | 9/1977 | Koberstein et al. | 260/601 R |
| 4,225,516 | 9/1980 | Biola et al. | 568/41 |
| 4,319,047 | 3/1982 | Komorn et al. | 568/41 |
| 5,015,776 | 5/1991 | Sandler | 568/41 |
| 5,155,262 | 10/1992 | Etzkorn et al. | 562/532 |
| 5,183,936 | 2/1993 | Etzkorn et al. | 562/532 |
| 5,198,578 | 3/1993 | Etzkorn et al. | 562/532 |
| 5,532,837 | 7/1996 | Hsu et al. | 568/41 |

FOREIGN PATENT DOCUMENTS

| | | |
|---|---|---|
| 797873 | 10/1968 | Canada . |
| 820968 | 8/1969 | Canada . |
| 2314917 | 1/1970 | France . |
| 48-56144 | 11/1973 | Japan . |
| 6809647 | 1/1970 | Netherlands . |
| 850 95 | 10/1984 | Romania . |
| 019954 | 6/1994 | Thailand . |
| 1150252 | 4/1969 | United Kingdom . |
| 1162054 | 8/1969 | United Kingdom . |
| 1166961 | 10/1969 | United Kingdom . |
| 1173174 | 12/1969 | United Kingdom . |
| 1177470 | 1/1970 | United Kingdom . |

OTHER PUBLICATIONS

PCT/US93/08552 International Search Report dated Nov. 17, 1993.

Pierson et al., "Synthesis of DL–Methionine", vol. 70, pp. 1450–1451 (1948).

Hickenbottom, W.J., "Reactions of Organic Compounds", pp. 381–383 (1957).

*Primary Examiner*—James H. Reamer
*Attorney, Agent, or Firm*—Senniger, Powers, Leavitt & Roedel

[57] ABSTRACT

A process for the continuous preparation of 3-(methylthio) propanal. A liquid reaction medium is contacted with a gaseous acrolein feed stream in a gas/liquid contact zone. The reaction medium contains 3-(methylthio)propanal, methyl mercaptan and a catalyst for the reaction between methyl mercaptan and acrolein. The gaseous acrolein feed stream comprises acrolein vapor and non-condensable gas. Acrolein is transferred from the acrolein feed stream to the reaction medium and reacts with methyl mercaptan in that medium to produce a liquid reaction product containing 3-(methylthio)propanal. The non-condensable gas is separated from the liquid reaction product. The reaction product is divided into a product fraction and a circulating fraction, and the circulating fraction is recycled to the gas/liquid contact zone.

6 Claims, 6 Drawing Sheets

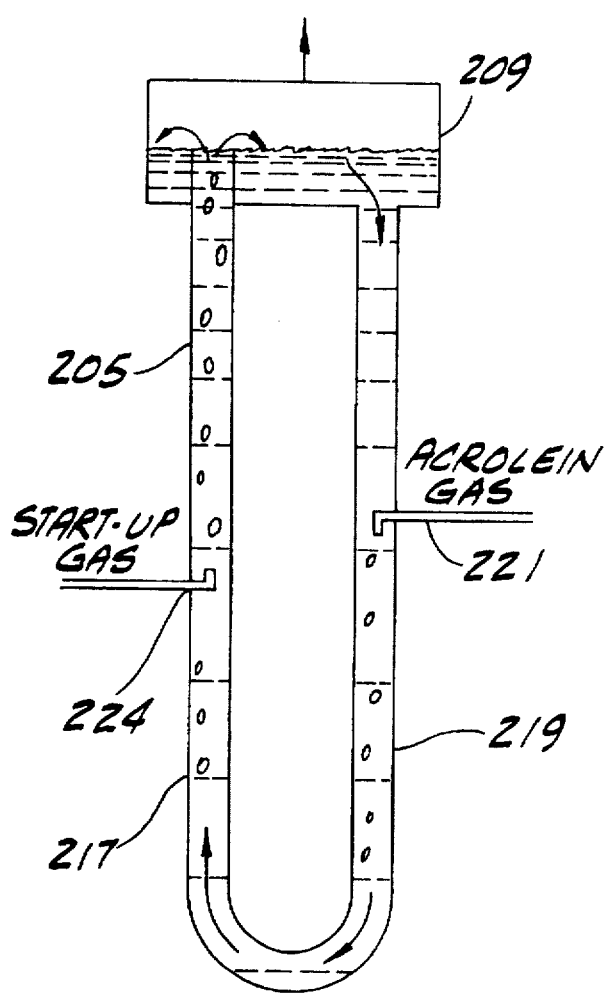
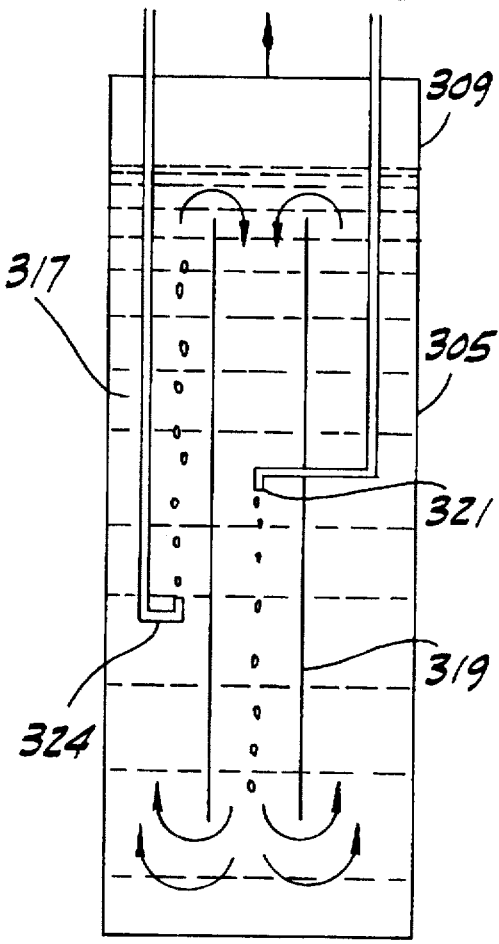

5,744,647

PROCESS FOR THE PREPARATION OF 3-(METHYLTHIO) PROPANAL

This is a continuation of application Ser. No. 08/557,699, filed Nov. 13, 1995, which is a continuation of Ser. No. 08/273,216, filed Jul. 11, 1994, now abandoned, which is a continuation-in-part of Ser. No. 08/073,763, filed Jun. 8, 1993 now U.S. Pat. No. 5,352,837.

BACKGROUND OF THE INVENTION

This invention relates to the preparation of 3-(methylthio) propanal, and more particularly to a continuous process for the direct manufacture of 3-(methylthio)propanal in a gas/liquid reaction system.

3-(Methylthio)propanal (hereinafter "MMP") is an intermediate for the manufacture of both d,l-methionine and 2-hydroxy-4-(methylthio)butanoic acid ("HMBA"). Methionine is an essential amino acid in which components of the animal feed compositions are commonly deficient. HMBA provides a source of methionine, and is widely used as a methionine supplement in animal feed formulations. MMP relatively free of impurities is typically required for the manufacture of HMBA or methionine.

MMP is produced by reaction of acrolein with methyl mercaptan. In a conventional process for the preparation of MMP, liquid acrolein and methyl mercaptan are introduced into a reactor containing liquid phase MMP product. Reaction takes place in the liquid phase. In order to produce MMP of desired quality, refined acrolein is used in the process, and/or the MMP product is distilled before use in the manufacture of either HMBA or methionine.

Acrolein is a highly toxic and flammable material. It is conventionally prepared by vapor phase oxidation of propylene over a solid phase catalyst, producing a crude gaseous reaction product which contains water vapor, acrylic acid, acetaldehyde, and other organic by-products. Typically, the gas is treated to remove acrylic acid, then contacted with refrigerated water for absorption of acrolein. The resultant aqueous solution is distilled to recover the absorbed acrolein and other organic components. The crude acrolein is then refined to reject lower boiling impurities such as acetaldehyde, producing a purified liquid acrolein product. The refined liquid acrolein is stored for use in the manufacture of MMP.

Storage of liquid acrolein involves significant toxicity, fire and explosion hazards. High capital and operating costs are consequently incurred in providing for the safe handling of this material. The cost of handling acrolein could be substantially reduced if gas phase acrolein were transferred directly and continuously from the acrolein manufacturing process to the MMP reactor without storage or condensation. However, since the conventional commercial processes for the preparation of MMP involve liquid phase reactions, the need to condense the gaseous acrolein product has been considered unavoidable. Moreover, because the conventional process typically uses a batch reaction system, condensation and in-process storage of liquid acrolein is necessary as a surge buffer between operation of the acrolein process and the MMP reactor.

Netherlands patent No. 6809647 describes a process in which acrolein is produced by catalytic oxidation of propylene and the acrolein-containing reaction gas mixture is passed to a vertical reaction column in which MMP is formed. MMP is circulated through the reaction column and both the acrolein-containing gas and methyl mercaptan are added near the bottom. MMP exiting the column contains a separate aqueous phase which is removed in a separator. MMP from the separator is partially recycled to the reaction column. A sodium bicarbonate solution is supplied to the circulating MMP. MMP product removed from the circulating reaction system is distilled at a pressure of 100 mmHg.

U.S. Pat. No. 4,225,516 describes a continuous process for the manufacture of MMP from the acrolein product gas obtained in the catalytic oxidation of propylene. In this process, the gas is first treated for removal of acrylic acid, then cooled to condense water vapor. To reduce the water vapor content to a level acceptable in the MMP reaction, the final condensation temperature is 0° to −5° C. The treated and cooled acrolein gas stream is contacted with a stream of liquid MMP in a countercurrent absorption tower, resulting in absorption of acrolein in the MMP. The MMP liquid stream containing dissolved acrolein is circulated to an MMP reactor where methyl mercaptan is added. The process proceeds by reaction of methyl mercaptan with MMP to form the hemimercaptal of MMP, and the hemimercaptal in turn reacts with acrolein in the liquid phase to produce additional MMP. Thus, the process requires the presence of up to 1% by weight of the hemimercaptal in the reaction mixture. MMP product is withdrawn from the system at a rate equivalent to MMP production in the reactor, while the bulk of the MMP stream is recirculated to the acrolein absorber.

To provide for quantitative absorption of acrolein in MMP, the '516 patent requires cooling the circulating MMP to a temperature 0° to −15° C. before it enters the absorber. The refrigeration required for condensing water vapor at 0° to −5° and cooling MMP to as low as −15° C. contributes substantially to the capital and operating expense of the '516 patent process. Moreover, because the reaction proceeds through formation of the hemimercaptal, the kinetics of the conversion reaction are relatively slow, resulting in less than desirable productivity and thus further adding to the cost of operation of the process.

Although sub-zero absorption increases acrolein recovery at equilibrium, it also increases the absorption of impurities, such as acetaldehyde, in the MMP product. Moreover, since the scrubber is separate from the reactor, acrolein absorbed in the scrubber is not consumed immediately in the absorption zone. As a consequence, acrolein tends to accumulate in the liquid phase, which decreases the driving force for mass transfer. The high concentration of acrolein in MMP liquid also increases the possibility of forming by-products from reactions between acrolein and MMP.

SUMMARY OF THE INVENTION

Among the several objects of the present invention are the provision of an improved process for the preparation of MMP; the provision of such a process which can be operated in a continuous mode; the provision of such a process which can be operated with high productivity; the provision of such a process which can be operated with a relatively crude acrolein raw material; the provision of such a process which does not require refrigeration for absorption or condensation of acrolein; the provision of such a process which eliminates the need for storage of liquid acrolein, in particular, the provision of such a process which can be operated using a gaseous acrolein feed obtained directly from the continuous oxidation of propylene or other suitable hydrocarbon; the provision of such a process which can be operated without formation of a separate aqueous phase in the MMP reaction mixture; and the provision of such a process which can produce high quality MMP for direct use in the preparation of methionine or HMBA without the need for further purification.

Briefly, the invention is directed to a process for the continuous preparation of MMP in which a liquid reaction medium is contacted with a gaseous acrolein feed stream in a gas/liquid contact zone. The reaction medium contains MMP, methyl mercaptan and a catalyst for the reaction between methyl mercaptan and acrolein. The gaseous acrolein feed stream comprises acrolein vapor and non-condensable gas. The relative proportions of acrolein and methyl mercaptan entering the contact zone are substantially stoichiometrically equivalent. Acrolein is transferred from the feed stream to the reaction medium and reacts directly with methyl mercaptan in the medium, without substantial formation of the intermediate hemi(methylthio)acetal of MMP, to produce a liquid reaction product containing MMP. Non-condensable gas is separated from the liquid reaction product, the reaction product is divided into a product fraction and a circulating fraction, and the circulating fraction is recycled to the gas/liquid contact zone. Acrolein and methyl mercaptan react in the liquid medium in a reaction zone that comprises the gas/liquid contact zone and a circulation zone into which the liquid reaction product is discharged from the gas/liquid contact zone and through which the circulating fraction is circulated back to the gas/liquid contact zone. Methyl mercaptan is introduced into the reaction zone at a location or locations such that no excess of methyl mercaptan prevails in any region of the reaction zone for time long enough for substantial formation of the intermediate hemi(methylthio)acetal.

The invention is further directed to a process for the continuous preparation of MMP in which a liquid reaction medium is contacted with gaseous acrolein feed stream in a gas/liquid contact zone. The reaction medium contains MMP, methyl mercaptan, and a catalyst for the reaction between methyl mercaptan and acrolein. The gaseous acrolein feed stream comprises acrolein vapor, non-condensable gas, and water vapor. Acrolein is transferred from the feed stream to the reaction medium and reacts with methyl mercaptan in the medium to produce a liquid reaction product containing MMP. The ratio of water vapor to acrolein in the acrolein feed stream is such that no substantial second liquid phase is present in the liquid reaction product as a result of condensation of water in the feed stream. Non-condensable gas is separated from the liquid reaction product, the reaction product is divided into a product fraction and a circulating fraction, and the circulating fraction is recycled to the gas/liquid contact zone.

The invention is also directed to a process for the continuous preparation of MMP in which a liquid reaction product is contacted with a gaseous acrolein feed stream in a gas/liquid contact zone, the reaction medium containing MMP, methyl mercaptan and a catalyst for the reaction between methyl mercaptan and acrolein. The gaseous acrolein feed stream comprises acrolein vapor, non-condensable gas, and water vapor. Acrolein is transferred from the feed stream to the reaction medium and reacts with methyl mercaptan in the medium to produce the liquid reaction product containing MMP. The molar ratio of water vapor to acrolein in the acrolein feed stream is not greater than about 0.3. The non-condensable gas is separated from the liquid reaction product, the reaction product is divided into a product fraction and a circulating fraction, and the circulating fraction is recycled to the gas/liquid contact zone.

Also contemplated by the invention is a process for the continuous preparation of MMP in which a liquid reaction medium is contacted with the gaseous acrolein feed stream in a gas/liquid contact zone through which the feed stream and the reaction medium are passed countercurrently. The reaction medium contains MMP, methyl mercaptan, and a catalyst for the reaction between methyl mercaptan and acrolein. The gaseous acrolein feed stream comprises acrolein vapor and non-condensable gas, whereby acrolein is transferred from the feed stream to the reaction medium and reacts with methyl mercaptan in the medium to produce a liquid reaction product containing MMP. The liquid hold-up in the countercurrent gas/liquid contact zone is sufficient to effect conversion in the gas/liquid contact zone of at least 90% of the acrolein contained in the feed gas. The non-condensable gas is separated from the liquid reaction product, the reaction product is divided into a product fraction and a circulating fraction and the circulating fraction is recycled to the gas/liquid contact zone.

The invention is also directed to a process for the continuous preparation of MMP in which a liquid reaction medium is contacted with a gaseous acrolein feed stream in a gas/liquid contact zone, the reaction medium containing MMP, methyl mercaptan and a catalyst for the reaction between methyl mercaptan and acrolein. The gaseous acrolein feed stream comprises acrolein vapor and non-condensable gas. Acrolein is transferred from the feed stream to the reaction medium and acrolein and methyl mercaptan are reacted in the reaction medium in a first reaction zone comprising the gas/liquid contact zone, producing an intermediate liquid reaction product. The non-condensable gas is separated from the intermediate liquid reaction product, the intermediate liquid reaction product is divided into an intermediate product fraction and a circulating fraction, and the circulating fraction is recycled to the gas/liquid contact zone. The first reaction zone comprises the gas/liquid contact zone and a circulation zone into which the liquid reaction product is discharged from the gas/liquid contact zone and through which the circulating fraction is circulated back to the gas/liquid contact zone. The intermediate product fraction is passed through a plug flow reactor to convert residual acrolein and methyl mercaptan to MMP.

Further contemplated by the invention is a process for the continuous preparation of MMP in which a liquid reaction product is contacted with the gaseous acrolein feed stream in a gas/liquid contact zone. The reaction medium contains MMP, methyl mercaptan, and a catalyst for the reaction between methyl mercaptan and acrolein. The gaseous acrolein feed stream comprises acrolein vapor, non-condensable gas and acrylic acid vapor. Acrolein is transferred from the feed stream to the liquid reaction medium and reacts with methyl mercaptan in the medium to produce a liquid reaction product containing MMP. The molar ratio of acrylic acid vapor to acrolein in the acrolein feed stream is not greater than about 0.1. Non-condensable gas is separated from the liquid reaction product, the reaction product is divided into a product fraction and a circulating fraction, and the circulating fraction is recycled to the gas/liquid contact zone.

The invention is also directed to a process for the continuous preparation of MMP in which acrolein vapor is produced by a vapor phase catalytic oxidation of a hydrocarbon to produce a crude acrolein reaction product stream. The crude acrolein reaction product stream is cooled to condense water vapor and acrylic acid therefrom and produce a cooled acrolein gas stream for conversion to MMP, the feed stream comprising acrolein and non-condensable gas. A liquid reaction medium is contacted with a gaseous acrolein feed stream comprising said cooled acrolein gas stream in a gas/liquid contact zone in which the total pressure is not greater than about 3 atmospheres. The reaction medium contains MMP, methyl mercaptan and a catalyst for the reaction between methyl mercaptan and acrolein. Acrolein is transferred from the feed stream to the reaction medium and reacts with methyl mercaptan in the medium to produce a liquid reaction product containing MMP. Non-condensable gas is separated from the liquid reaction product, the reaction product is divided into a product fraction and a circulating fraction, and the circulating fraction is recycled to the gas/liquid contact zone.

The invention is further directed to a process for the continuous preparation of MMP in which a crude reaction product gas stream obtained from the catalytic oxidation of of a hydrocarbon is cooled, thereby producing a cooled gas stream comprising acrolein and a condensate comprising water, acrylic acid and a residual proportion of acrolein. The condensate is separated from the cooled gas stream and the condensate is fractionally distilled to produce an overhead fraction comprising acrolein and a bottoms fraction which is substantially free of acrolein. The overhead fraction is mixed with the cooled gas stream to produce a combined acrolein stream. A liquid reaction medium is contacted with a gaseous acrolein feed stream in a gas/liquid contact zone. The reaction medium contains MMP, methyl mercaptan and a catalyst for the reaction between methyl mercaptan and acrolein. The gaseous acrolein feed stream comprises the combined acrolein gas stream and contains acrolein, non-condensable gas, and water vapor. Acrolein is transferred from the feed stream to the reaction medium and reacts with methyl mercaptan in the medium to produce a liquid reaction product containing MMP. Non-condensable gas is separated from the liquid reaction product, the reaction product is divided into a product fraction and a circulating fraction, and the circulating fraction is recycled to the gas/liquid contact zone.

The present invention is also directed to a process for the continuous preparation of 3-(methylthio)propanal. The process comprises contacting a liquid reaction medium with a gaseous acrolein feed stream in a gas/liquid contact zone of a reaction zone. The reaction medium contains 3-(methylthio)propanal, methyl mercaptan, and a catalyst for the reaction between methyl mercaptan and acrolein. The gaseous acrolein feed stream comprises acrolein vapor and noncondensable gas. The gaseous acrolein feed stream and the reaction medium are caused to flow co-currently through the gas/liquid zone. Acrolein is transferred from the feed stream to the reaction medium and reacts with methyl mercaptan in the medium to produce a liquid reaction product containing MMP. Noncondensable gas is separated from the liquid reaction product and the reaction product is divided into a product fraction and a circulating fraction. The circulating fraction is recycled to the gas/liquid contact zone. The heat of reaction is removed from the reaction zone by indirect transfer of heat from said liquid reaction medium to another fluid. The rate of circulation of the liquid medium and the location from which heat is removed from the reaction zone are such that the temperature of the liquid reaction medium does not vary more than about +5F throughout said reaction zone.

Other objects and features will be in part apparent and in part pointed out hereinafter.

BRIEF DESCRIPTION OF THE DRAWINGS

FIG. 3 is a schematic illustration of a gas lift reactor adapted for operation at low pressure drop;

FIG. 4 is a schematic illustration of a draft tube type gas lift reactor adapted for operation at low pressure drop;

DESCRIPTION OF THE PREFERRED EMBODIMENTS

In accordance with the present invention, MMP is produced from methyl mercaptan and a gaseous acrolein feed stream in a gas/liquid reaction system comprising liquid MMP. In a gas/liquid contact zone, a liquid phase containing MMP and catalyst is contacted with methyl mercaptan and a gas containing acrolein and non-condensables. Acrolein is transferred from the gas phase to the liquid phase, and reacts directly with methyl mercaptan in the liquid phase to produce additional MMP. Exothermic reaction heat is removed to a heat transfer fluid flowing through heat transfer means, such as a jacket or coil, in contact with the gas/liquid contact zone, or in an MMP circulating loop between the liquid exit and liquid inlet of the contact zone.

In the gas/liquid contact zone, high mass transfer coefficients are provided by intimate gas/liquid contact, and the driving force for mass transfer is preferably maximized by maintaining substantially plug flow in the gas phase. Intimate gas/liquid contact may be realized by operating in a turbulent flow range, which may be characterized, for example, by relatively high superficial gas and liquid velocities in a bubble flow regime, wherein bubbles are actively coalescing and breaking up as a result of the turbulence. Such turbulent conditions also promote high rates of heat transfer from the gas/liquid contact zone to a jacket or coil in heat transfer communication with the contact zone. Alternatively, gas/liquid contact may be effected by countercurrent flow of gas and liquid within the contact zone. In the latter embodiment of the invention, reaction heat is advantageously transferred to a cooling fluid in an external heat exchanger through which the MMP reaction medium is circulated.

By maintaining substantially equimolar addition of methyl mercaptan and acrolein to the reaction medium, formation of the hemithioacetal of MMP is substantially avoided. As a consequence, the methyl mercaptan and acrolein react directly to form MMP. Since this reaction path is much faster than the reaction which proceeds through formation of the hemithioacetal, the rate of reaction is 3 to 10 times higher than that obtained in a process of the type described in the '516 patent. At the reaction rates obtained in the novel process, the rate of conversion is limited by the rate of mass transfer of acrolein from the gas phase to the liquid phase. However, it has been found that, when turbulent conditions are maintained in accordance with the preferred embodiments of the invention, high coefficients of mass transfer are realized. Moreover, because of the direct rapid reaction between acrolein and methyl mercaptan in the liquid phase, acrolein entering the liquid phase is consumed immediately, thereby enhancing the driving force for mass transfer. Thus, overall mass transfer rates are high. The combined effect of direct reaction and high mass transfer rates affords high productivity in the reaction system of the invention.

Figure 1:
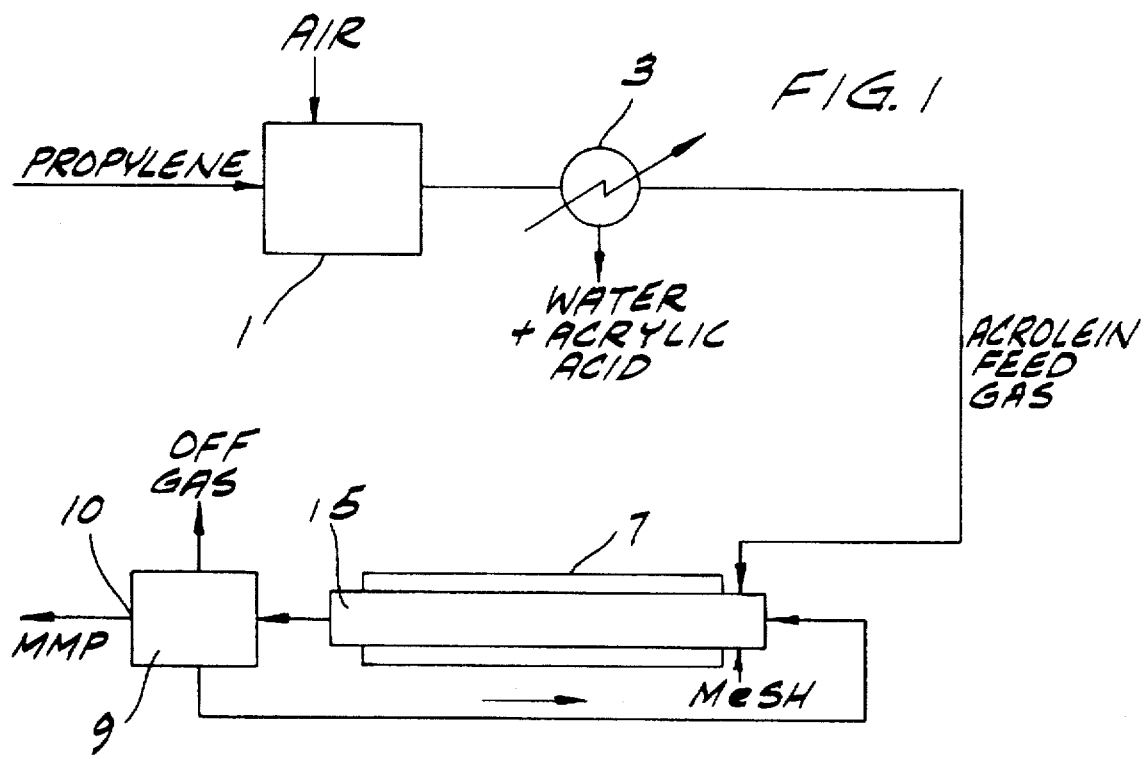
FIG. 1 is a schematic flowsheet of the process of the invention, illustrating continuous manufacture of MMP from a crude gaseous acrolein product obtained from the continuous catalytic oxidation of propylene.

Referring to FIG. 1, acrolein is continuously generated in an acrolein reactor 1 by catalytic oxidation of propylene, propane or other suitable hydrocarbon feedstock in the presence of steam and non-condensable gas. Where the feedstock is propylene, the crude acrolein product gas exiting the reactor contains about 4% to about 10% by volume acrolein, between about 0.3% and about 1.0% by volume acrylic acid, up to about 1.0% by volume propylene, up to about 1.0% by volume propane, up to about 0.5% by volume propionaldehyde, between about 0.1% and about 0.4% by volume acetaldehyde, and between about 30% and about 50% by volume water vapor, and between about 40% and about 55% by volume non-condensables, including oxygen, nitrogen, carbon monoxide and carbon dioxide. The crude product gas is then treated to substantially reduce the water vapor and acrylic acid content thereof. Preferably, the crude product is treated by cooling it in an indirect heat exchanger 3, causing condensation of acrylic acid and water from the crude gas product. Although refrigerated water may be used as the cooling fluid in heat exchanger 3, ambient temperature water, e.g., city water, well water or cooling tower water, can be economically used. Condensation of acrylic acid and water in a heat exchanger using ambient temperature water as the cooling medium provides a cooled acrolein feed gas stream containing: between about 5% and about 25%, more commonly between about 7% and about 15%, by volume acrolein; up to about 0.1%, more preferably up to about 0.01%, by volume acrylic acid; up to about 2.0% by volume propylene; up to about 1.0% by volume propane; up to about 1.0% by volume propionaldehyde; up to about 0.5% by volume acetaldehyde; between about 1 and about 8%, more preferably between about 1% and about 3%, by volume water vapor; and between about 60% and about 80% by volume non-condensables. Preferably, the molar ratio of water vapor to acrolein in the cooled gas stream is between about 0.05 and about 0.3, more preferably between about 0.05 and about 0.15, and the molar ratio of acrylic acid to acrolein is between 0 and about 0.01, more preferably between 0 and about 0.001. Optionally, acrylic acid may be initially removed from the crude acrolein product gas by contacting the gas with a conventional absorbing agent in a countercurrent contacting unit, such as a packed tower. Gas exiting the absorber may be further cooled for condensation of water vapor by passing the gas through an indirect heat exchanger downstream of the absorber.

The cooled acrolein feed gas stream is then introduced into a reaction medium, comprising a circulating stream of MMP, in a continuous flow reactor 5. Reactor 5 is provided with a cooling jacket 7. The circulating MMP contains a catalyst for the reaction of methyl mercaptan and acrolein. Catalyst can be injected continuously or intermittently at any convenient location in the loop. Methyl mercaptan is introduced into the MMP circulating stream at any convenient point, but is preferably introduced together with the acrolein, or slightly upstream of the point at which acrolein is introduced. Thus, a two phase reactant mixture is prepared, in which acrolein is distributed between a liquid phase containing MMP and catalyst, and a gas phase containing non-condensables. Methyl mercaptan may also be distributed between the two phases, but is observed to be substantially dissolved in the liquid phase. The catalyst is typically an organic acid salt of an amine. In the gas/liquid contact zone, which extends downstream from the point of introduction of acrolein, acrolein is progressively transferred from the gas phase to liquid phase, and reacts directly and continuously with methyl mercaptan in the liquid phase to produce MMP. To the extent that methyl mercaptan is initially distributed between the phases, it is also progressively transferred to the liquid for reaction with acrolein.

Water vapor contained in the acrolein feed gas may also condense in the MMP stream in the gas/liquid contact zone. By cooling the crude acrolein reaction product gas upstream of the reactor 5 to partially condense water vapor, the molar ratio of water vapor to acrolein is maintained low enough so that no substantial second (aqueous) liquid phase is formed in the gas/liquid contact zone; nor is any second liquid phase present in the gas/liquid contact zone or liquid reaction product due to separation of an aqueous phase from the MMP reaction medium anywhere in the reaction system. Preferably, the water content of the circulating MMP medium is not more than about 6% by weight, and is typically between about 1% and about 6% by weight. At the preferred temperatures for the reaction, as discussed hereinbelow, water in these concentrations remains fully dissolved in the MMP phase. As noted above, the molar ratio of water vapor to acrolein in the feed gas stream is no greater than about 0.3. This ratio has been determined to be sufficient to control the water content of the MMP circulating medium at a concentration low enough to avoid formation of a separate aqueous phase at the temperatures prevailing at the liquid exit of the gas/liquid contact zone.

The presence of excessive amounts of acrylic acid in the MMP product is also avoided by cooling of the crude acrolein reaction gas with ambient temperature water. Condensation of acrylic acid from the crude gas stream in the cooler provides a gaseous acrolein feed stream to the MMP reactor in which the molar ratio of acrylic acid to acrolein in the feed stream is not more than about 0.01, preferably not more than about 0.001, and the acrylic acid vapor concentration is not greater than about 0.1%, preferably not more than about 0.01%.

Turbulent flow conditions are maintained in the gas/liquid contact zone, preferably by establishing a two phase flow velocity in the turbulent region, as defined above. Reaction progresses rapidly to produce a two phase reaction product mixture, comprising a liquid phase containing MMP product and catalyst, and a gas phase containing non-condensables. The reaction product exiting the reactor is introduced into a separator 9 where the gas phase and liquid phase are allowed to separate. The gas phase, which contains propane, propylene, propionaldehyde, acetaldehyde, and water vapor, is vented from the separator to an emissions control device, such as an incinerator. Where the vent gas contains any substantial amount of unabsorbed acrolein or unreacted propylene, it may be feasible to recycle a portion of the vent gas to a propylene oxidation reactor. However, the combination of high mass transfer rates in the gas/liquid contact zone and substantially equimolar addition of acrolein and methyl mercaptan to the reaction system produces a vent gas stream which typically contains between about 90% and about 97% by volume non-condensables and only between about 0.01% and about 0.03% by volume acrolein. Typically, the vent gas also contains between about 1% and about 2% propylene, an amount suitable for fueling a flare through which the noncondensables and residual organic vapors can be purged from an integrated acrolein/MMP manufacturing facility. Alternatively, a portion of the vent gas stream may be recycled to provide a source of water vapor and non-condensable gas to the propylene oxidation reactor.

Net production of MMP is removed from the separator via a product port 10, while the bulk of the MMP is recirculated from the separator to the reactor. The MMP product is substantially free of methyl mercaptan, acrolein and the impurities contained in the acrolein feed gas. Without need for further purification, the MMP product may be used as an intermediate in the manufacture of HMBA.

The reaction may be carried out at a temperature between about 30° C. and about 70° C., preferably between about 40° C. and about 50° C., and at a total pressure of between about 1 and about 3 atmospheres, preferably between about 1.5 and about 2 atmospheres. Methyl mercaptan and acrolein are introduced into the reaction medium in a mercaptan to acrolein molar ratio of between about 0.95 and about 1.2, but most preferably between about 1.00 and about 1.02. As noted, the acrolein feed contains between about 5% and about 25% by volume, more typically between about 7% and about 15% by volume, acrolein. Most preferably the acrolein vapor feed stream contains between about 10% and about 15% by volume acrolein.

At reaction temperatures below about 50° C., the favorable acrolein equilibrium between the liquid and gas phases provides a particularly effective driving force for mass transfer to the liquid phase, but at temperatures significantly below 40° C. a refrigerated coolant fluid may be necessary, and the kinetics of reaction may begin to limit productivity. Moreover, at cooler reaction temperatures the equilibrium distribution of acetaldehyde between the gas and liquid phases also becomes unfavorable, resulting in an increased concentration of acetaldehyde in the product exiting the separator. An especially preferred temperature for the reaction is between about 40° C. and about 45° C. In this range, the reaction temperature can be readily controlled by transfer of heat from the reacting mixture to cooling tower water at up to 35° C. flowing through a jacket surrounding the gas/liquid contact zone. As the reaction consumes dissolved acrolein, additional acrolein is progressively transferred from the gas to the liquid phase in response to the disequilibrium caused by the acrolein consumption. Consequently, in most embodiments of the present invention, refrigeration is not needed or desired for either controlling the reaction temperature or promoting transfer of acrolein from the gas to the liquid phase.

Although high pressure also favors mass transfer, rapid mass transfer is achieved at or near atmospheric pressure in a turbulent gas/liquid contact zone, so that the use of high pressure reactor vessels is not necessary. Moreover, by maintaining the reactor at moderate pressure levels, the pressure prevailing in the propylene oxidation reactor may be sufficient for introduction of the acrolein product gas into the MMP reactor without the need for mechanical compression of the gas.

While it is feasible to operate with a gas feed stream having an acrolein content ranging between about 5% and about 25% by volume, the rate of mass transfer is enhanced if the feed gas contains at least about 10% by volume acrolein. On the other hand, too high an acrolein content may overload the absorptive capacity of the gas/liquid contact zone, and may have an adverse effect on both recovery of acrolein from the gas phase and yield of MMP based on acrolein. Further balancing the immediate needs of the present process with factors bearing on the operation of a typical acrolein reactor, a feed gas concentration of between about 10% and about 15% by volume acrolein may be considered optimal.

By establishing a very slight excess of mercaptan in the reactant mixture, conversion of acrolein is maximized and the need for disposition of unreacted acrolein is essentially obviated. Where the molar ratio of reactants is controlled in the range of between about 1.00 and about 1.02 moles methyl mercaptan per mole of acrolein, direct reaction between the mercaptan and acrolein is effected in preference to formation of the intermediate hemi(methylthio)acetal of MMP. As a consequence, a high rate of reaction is realized, with high productivity and relatively low capital and operating expense of the reactor. The reactant ratio may be controlled by various means known to the art. Preferably, the circulating MMP stream is periodically analyzed by gas chromatography downstream of the gas/liquid contact zone, and any necessary adjustments are made in the relative acrolein and methyl mercaptan feed rates to make certain that the proper excess of methyl mercaptan is maintained and formation of the hemithioacetal avoided. An in-line analyzer may be used for this purpose. Except during startup, the process is operated in a continuous recirculating steady state mode. Accordingly, the addition ratio of methyl mercaptan to acrolein can be adjusted to essentially to 1.0 as soon as steady state conditions are achieved.

Conventional catalysts and catalyst concentrations may be used for the reaction. Such catalysts include a wide variety of organic amines such as, for example, pyridine, hexamethylenetetramine, or triethylamine. Organic acids are typically included to inhibit polymerization of acrolein. Where, for example, a pyridinium acetate catalyst is used, the concentration is maintained at between about 0.2 and about 1.0%, preferably between about 0.35 and about 0.5%, by continuous or periodic additions of catalyst to the liquid phase.

The rate of MMP circulation is at least an order of magnitude greater than the rate of production of MMP, preferably between about 20 and about 50 times greater, so that a co-current flow reactor of the type illustrated in FIG. 1 is essentially backmixed in the liquid phase. Any of a variety of two phase reactors may be used in the reaction, e.g., a co-current flow pipeline reactor, a stirred tank reactor, or a countercurrent flow reactor such as a wetted-wall column, a bubble column, a packed column or a tray column. To promote rapid mass transfer, the gas phase is preferably in plug flow. In plug flow an acrolein concentration gradient in the gas phase is established and maintained along the reactant flow path in the gas/liquid contact zone, thereby providing an integrated average driving force for mass transfer substantially greater than that which prevails when the gas phase is backmixed. A gas lift reactor is particularly preferred because it may be operated in gas phase plug flow, and because the substantial volume of non-condensables in the acrolein gas feed stream can be used to advantage both for circulation of the MMP liquid phase and to produce excellent liquid mixing in the reactor. Thus, the need for mechanical moving parts, such as pumps or agitators, is eliminated. Alternatively, a countercurrent column may be used to particular advantage, especially where there is a need to minimize pressure drop through the gas/liquid contact zone.

Figure 2:
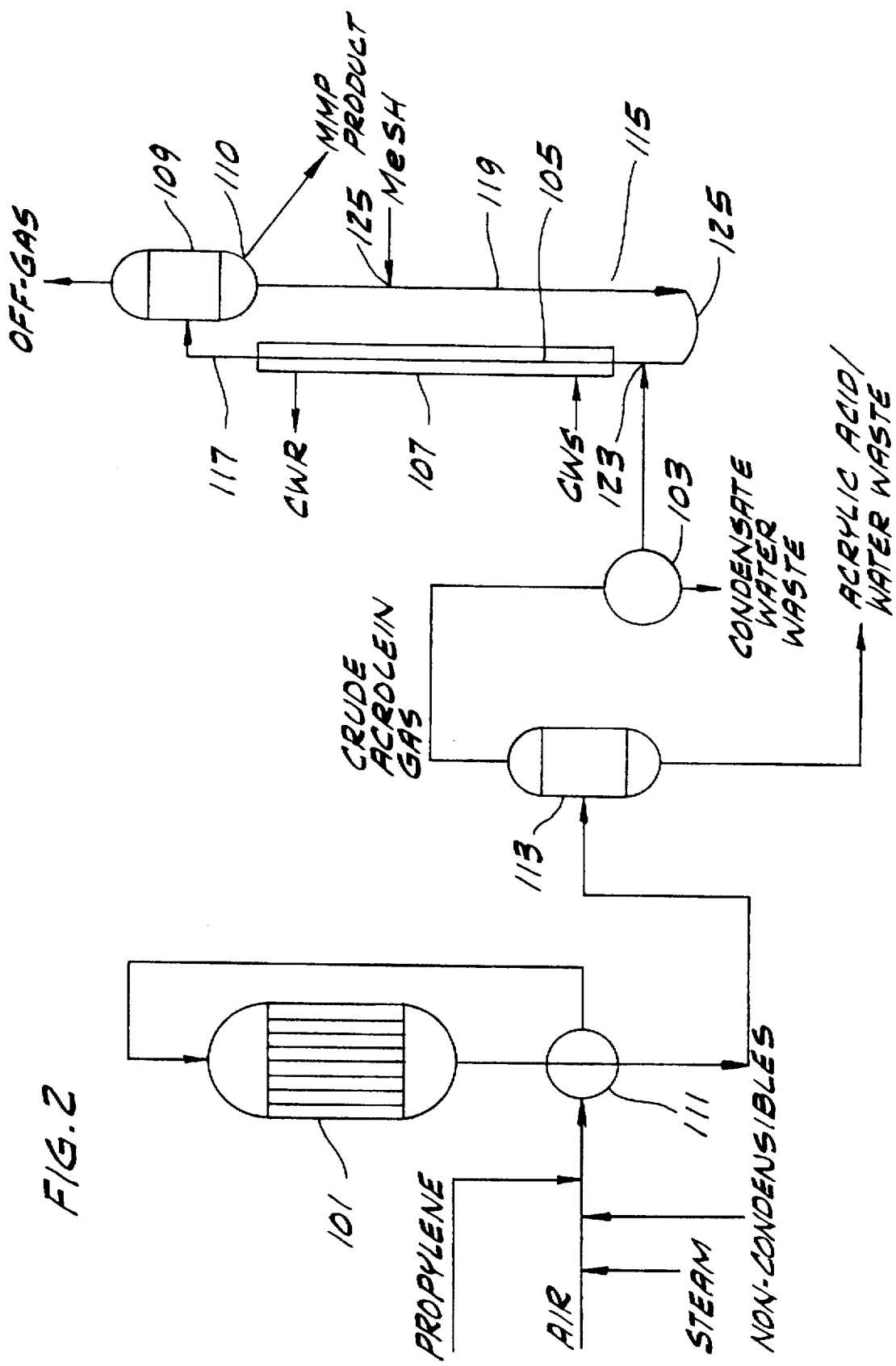
FIG. 2 is a schematic illustration of a preferred process of the invention in which MMP is produced from methyl mercaptan and acrolein in a turbulent gas lift reactor.

Illustrated in FIG. 2 is a loop type gas lift reactor apparatus of the invention and its use in an integrated process in which crude gas phase acrolein is cooled and introduced directly into the MMP reactor. In the integrated process as illustrated, propylene (or other suitable hydrocarbon) is mixed with air and introduced together with diluent steam and/or noncondensable gases into a reactor 101 containing a catalyst suitable for the oxidation of the hydrocarbon to acrolein. A reactor feed stream is prepared by mixing air and propylene with diluents as noted, and this mixture is preheated in an indirect heat exchanger 111 by transfer of heat from the crude acrolein product gas. In a countercurrent flow packed tower absorber 113, the partially cooled product gas is contacted with a liquid absorbing medium for removal of acrylic acid from the gas stream. Gas exiting the absorber is passed through another indirect heat exchanger 103 for further cooling of the product gas and condensation of acrylic acid and water vapor therefrom. Optimally, and preferably, acrylic acid and excess water vapor are removed by condensation alone, obviating the need for the acrylic acid absorber and the pressure drop required for gas flow through the absorber. The cooled acrolein product gas is then introduced into the gas lift reactor 105.

Reactor 105 comprises an upward flow conduit ("upleg") 117 provided with a jacket 107 through which a cooling fluid may be circulated. The reactor further comprises a downflow conduit ("downleg") 119 which is in fluid flow communication with the upleg through a bottom loop 121. Upleg 117 comprises the gas/liquid contact zone. Between and in fluid flow communication with the upper ends of the two legs is a separator 109. Downleg 119, bottom loop 121 and separator 109 together constitute a circulation zone in which reaction between acrolein and methyl mercaptan may continue after the reaction medium exits the gas/liquid contact zone. Thus the reaction zone comprises both the gas/liquid contact zone and the circulation zone. The rate of circulation and the location of jacket 107 are such that the temperature of the MMP liquid reaction medium does not vary more than about ±5° C. throughout the reaction zone, preferably not more than about ±2° C. in the upleg of the reactor.

In a commercial unit, desired capacity may be provided by the use of multiple reactor loops, in combination with a single separator. Upleg 117 includes a gas inlet 123 at the lower end thereof for introduction of cooled acrolein feed gas, and downleg 119 has a fluid inlet 125 for introduction of vapor or liquid methyl mercaptan. Alternatively, the methyl mercaptan can be introduced at or near the point of introduction of acrolein feed gas. Catalyst can be injected continuously or intermittently at any convenient point. Preferably, the feed points of acrolein and methyl mercaptan are sufficiently proximate so that, in whatever portion of the reaction zone between the feed points in which the MMP medium may contain an excess of methyl mercaptan, the residence time of circulating MMP medium is not sufficient for substantial formation of the hemimercaptal at the ratio of methyl mercaptan to acrolein and absolute methyl mercaptan concentration prevailing therein. In a gas lift reactor, the concentration of methyl mercaptan and any excess over the concentration of acrolein are insignificantly small due to the dilution effect of the large recirculating MMP flow in the loop. The upleg comprises the gas/liquid contact zone and is sized so that two phase flow is in the bubble flow regime, wherein the gas is dispersed in the form of discrete bubbles within a continuous liquid phase, or at the margin between bubble flow and slug flow. Liquid circulation is induced by the liquid head differential resulting from the lower density of the two phase fluid contained in the upleg as compared to the liquid in the downleg. To establish the preferred flow conditions, the superficial gas velocity in the upleg is adjusted to between about 0.1 and about 0.5 m/sec. At such combination of gas velocity and reactor height, the gas holdup in the upleg is between about 5% and about 20%, and the superficial liquid velocity in the upleg is between about 0.3 and about 3.0 m/sec. To provide for the desired rate of circulation, the height of the gas lift loop is preferably between about 20 feet and about 30 feet, requiring the gas pressure at the gaseous acrolein feed inlet to the reactor to be between about 10 and about 15 psig. i.e., between about 67 and about 100 kPa gauge. Optionally, a pump may be provided in bottom loop 121 to assist in circulation and lower the requisite height of upleg 117.

Especially satisfactory mass transfer from the gas to the liquid phase is achieved by controlling the superficial velocities of the gas and liquid phase in the upleg so that two phase flow is in the bubble flow regime. In bubble flow, the dispersion of the gas as small bubbles in a continuous liquid phase provides maximum area for mass transfer. Proper balancing of liquid and gas velocities maintains a stable bubble flow condition, and avoids coalescence of bubbles and slugging. The ranges of velocities effective for this purpose may be predicted with reasonable accuracy based on the principles illustrated, for example, by Govier and Aziz, "The Flow of Complex Mixtures in Pipes," Van Nostrand Reinhold Company, New York, 1972. See especially pp. 324 to 325 which illustrates flow patterns as a function of fluid velocities for air/water systems. Since flow patterns depend on fluid properties and pipe diameters, some routine experimentation may be required for corroboration of the optimum velocities for a particular system. It should be understood that the process of the invention can also be operated in a slug flow regime, but mass transfer is maximized by operating under turbulent bubble flow conditions.

To start up the reactor of FIG. 2, the circulating loop is substantially filled with MMP, after which introduction of acrolein feed gas and methyl mercaptan can be immediately commenced. Even at ambient temperature, the reaction proceeds at a sufficiently rapid rate so that exothermic heat of reaction rapidly brings the reactant mixture to the preferred 40° C.+temperature at which steady state operations are conducted.

Using a gas lift reactor, the process of the invention can be operated to provide an acrolein recovery of at least about 98%, a conversion of at least about 97%, and an acrolein yield of at least about 95%. Recovery is defined as the proportion of acrolein entering in the feed gas that is transferred to the liquid phase; conversion is defined as the proportion of entering acrolein which is consumed in the reaction; and yield is defined as the proportion of the acrolein in the feed gas which is converted to net product MMP.

When the process of the invention is operated in tandem with a facility in which acrolein is produced by catalytic oxidation of propylene, no increase in by-product formation or MMP product degradation is incurred as a result of the presence of impurities such as propylene, propane, acetaldehyde, propionaldehyde, oxygen, carbon monoxide, carbon dioxide, in the acrolein feed gas. Thus, the process can be economically integrated with an acrolein manufacturing facility to avoid the need for condensation of acrolein, purification of acrolein, or storage of acrolein in liquid form. The process is particularly adapted for use in combination with an acrolein manufacturing process in which the crude acrolein product gas comprises a mixture of acrolein vapor and inert gases containing low concentrations of water vapor and organic impurities.

Where a loop type gas lift reactor is used, the back pressure resulting from pressure drop in the upleg may tend to raise the pressure in the acrolein reactor to a level higher than optimum. This back pressure is at least partially offset by elimination of the acrolein absorber used in the preparation of refined liquid acrolein. Pressure drop across the absorber imposes back pressure on the propylene or other hydrocarbon oxidation reactor in a conventional acrolein process. Moreover, any adverse effect of pressure drop in a gas lift reactor may be avoided by any of a number of stratagems. For example, a modest negative pressure may be imposed on the separator 109 by placing a compressor in the gas vent line from the separator. As noted above, the requisite height of the gas/liquid contact zone may be reduced by mechanical circulation of the MMP reaction medium.

Illustrated in FIG. 3 is an alternative gas lift reaction system which is adapted for operation at especially low gas pressure drop. Instead of introducing acrolein gas near the bottom of the upleg, as in FIG. 2, the gaseous acrolein feed stream is introduced through an inlet 221 in downleg 219. Circulation in the gas lift reactor loop is initiated on startup by introduction of a startup gas through an inlet 224 in upleg 217. The elevation of the startup inlet is at least slightly lower than that of inlet 221, but both may be located as high as necessary in the gas loop so that liquid head in the loop does not create excessive backpressure at the point of gas introduction. Either the acrolein feed gas or an inert gas may be used for startup. Once circulation of the MMP reaction medium has been established, introduction of acrolein feed gas may be commenced through inlet 221, and introduction of startup gas terminated as soon as two phase flow extends from inlet 221 to inlet 224 or above. Methyl mercaptan can be introduced at any convenient point, e.g., at or near the acrolein feed point, or through the start-up gas line. Catalyst can be injected anywhere in the loop. The gas/liquid contact zone comprises the portion of downleg 219 below inlet 221 plus the entire upleg 217. The balance of the circulating loop comprises the circulation zone, and the gas/liquid contact zone and circulation zone together make up the reaction zone. Because the component of two phase zone in leg 217 is longer than that in leg 219, downward flow of the two phase reactant mixture is maintained in leg 219. The reactor then continues to operate with a liquid head differential determined by the liquid head above inlet 221. Where that liquid head is modest, pressure drop is minimized. If pressure drop limitations on permissible liquid head differential cause the superficial liquid velocity to be less than optimum for effective mass transfer, this can be compensated for by increasing the vertical dimension below the gas entry point to increase the residence time for mass transfer.

In another alternative, a draft tube type gas lift reactor may be used in which the acrolein feed gas is introduced into the draft tube. Such a system is illustrated in FIG. 4. The reactor 305 comprises a draft tube 319 radially centered in a cylindrical reaction vessel 309 and comprising the downleg of a gas lift reactor system. The annular region between draft tube 319 and the inside wall of reactor vessel comprises an upleg 317, and together the draft tube and annular region comprise a circuit for circulation of MMP. Gaseous acrolein feed stream is introduced through a dip pipe inlet 321 in draft tube 319. As will be apparent to those skilled in the art, and noted in connection with FIG. 3, methyl mercaptan and catalyst may be introduced at any convenient point in the loop. Circulation in the gas lift reactor loop is initiated on startup by introduction of a startup gas through an inlet 324 in annular upleg 317. Though shown as a dip pipe with a single outlet, inlet 324 is preferably a ring type sparger surrounding the draft tube, with outlets spaced around its entire periphery. As in the reactor of FIG. 3, the elevation of the startup inlet is at least slightly lower than that of inlet 321, and both may be located at whatever elevations are necessary to minimize backpressure. Circulation is commenced in the same manner as described above with respect to FIG. 3, after which introduction of acrolein feed gas may be commenced through inlet 321, and introduction of startup gas terminated as soon as two phase flow extends from inlet 321 to inlet 324. The longer two phase zone in the annular leg 317 maintains downward flow of the two phase reactant mixture in the draft tube. The reactor then continues to operate with a liquid head differential determined by the liquid head above inlet 321. Without significantly affecting the gas pressure drop, the vertical dimension of the draft tube below the dip tube outlet may be as large as necessary to provide adequate residence time for mass transfer. Reaction heat may be removed from the reactor of FIG. 3 via a jacket surrounding the reactor 305 or a coil or other heat transfer surface disposed within the reactor. Except for the superficial liquid velocity and residence time in those instances where liquid head differential is minimized to avoid excessive backpressure on the acrolein reactor, the preferred operating conditions for the reactor of FIG. 3 are substantially the same as those in FIG. 2.

Figure 5:
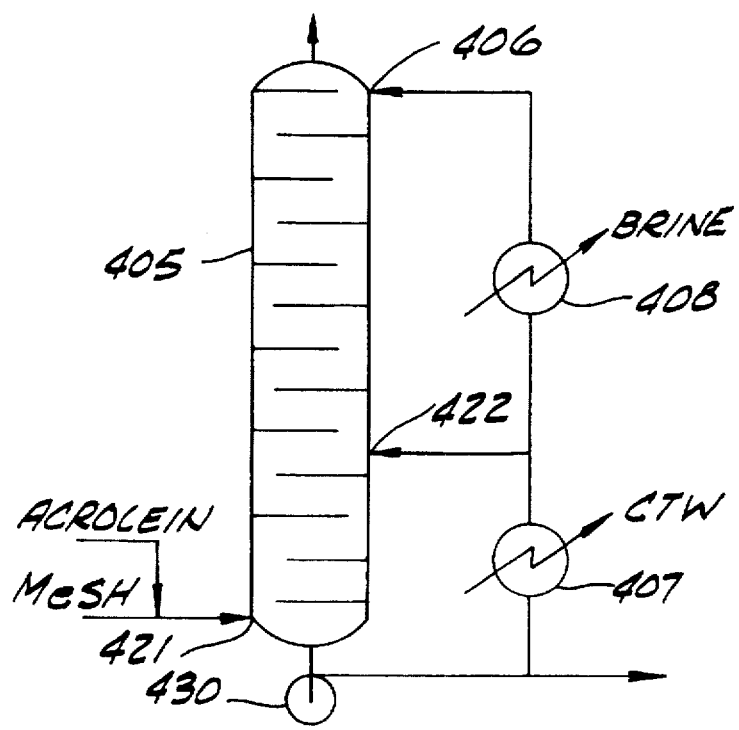
FIG. 5 is a schematic illustration of a tray column reactor for conversion of methyl mercaptan and acrolein to MMP.

Another preferred embodiment of the invention is illustrated in FIG. 5. In this embodiment, the reaction is conducted in a tray column 405 through which liquid MMP reaction medium is circulated. Liquid MMP is introduced through a liquid inlet 406 at the top of column and acrolein feed gas is introduced through a gas inlet 421 at the bottom. Methyl mercaptan is also introduced at or near the bottom of the column, preferably through the same inlet 421. The interior of the column comprises a gas/liquid contact zone through which the gas and liquid phases flow countercurrently to each other, mass transfer from the gas to the liquid phase occurring primarily on the trays of the column. Reaction takes place in the liquid phase on the trays, the downcomers between trays, and in the circulation zone comprising the sump at the bottom of the column and the recirculation path to liquid inlet 406. As the gas flows up the column, acrolein is progressively transferred to the liquid phase, so that gas exiting the top of the column is substantially free of acrolein and is vented through an incinerator, flare, or similar emissions control device.

Unlike the essentially isothermal gas lift reactors of FIGS. 2-4, the tray column reactor itself operates substantially adiabatically. Liquid reaction product mixture exits the bottom of the column and is divided into a product fraction which is removed from the process and a recirculating fraction which is cooled and returned to the column. A pump 430 provides the motive force for recirculation. Reaction heat is removed by transfer to cooling tower water in an indirect heat exchanger 407. In order to assure complete absorption of acrolein into the liquid phase, the recirculating MMP exiting heat exchanger 407 is preferably passed through a second indirect heat exchanger 408 where the recirculating stream is cooled to about 10° C. or lower, preferably about 0° to about 10° C., by transfer of heat to refrigerated brine. Optionally, a portion of the MMP fraction exiting cooler 407 may be recycled to port 422 at a tray in the lower portion of the column, e.g., the 6th or 8th actual tray in a 20 tray column. Although partial recycle to the lower portion of the column alters the column temperature profile, reaction occurs throughout the column in both that embodiment and in the embodiment wherein all circulating MMP reaction medium is recycled to the top of the column.

Because of the substantially adiabatic operation, a temperature gradient prevails within the column. The liquid stream within the column is preferably heated from a temperature of about 0° C. to about 10° C. at the top of the column to a temperature of about 50° C. to about 60° C. at the bottom. Because gas exiting the column is contacted by MMP at low temperature, a favorable equilibrium prevails and acrolein recoveries >99% can be realized. To promote reaction in the gas/liquid contact zone, the temperature of the liquid medium at the liquid exit of the column is preferably allowed to rise to at least about 40° C. The temperature rise of the liquid medium across the gas/liquid contact zone is preferably between about 20° and about 80° C. Because substantially the only gas pressure drop occurs in passage of gas through the liquid held by the trays, the tray column reactor may be designed to provide a very modest back pressure on the acrolein reactor.

In the system of FIG. 5, packing instead of trays may provide the means for promoting mass transfer between the gas and liquid phases. However, a tray tower is preferred because the countercurrent gas/liquid contact zone approximates plug flow conditions. A packed tower may be more subject to channeling and eddying which sacrifice the benefit of plug flow with respect to driving force for absorption and reaction, and further may fail to provide sufficient liquid holdup to allow the reaction to proceed substantially to completion in the liquid phase within gas/liquid contact zone. Incomplete reaction in the liquid phase also reduces the driving force for mass transfer, thereby reducing the overall rate of reaction in the gas/liquid contact zone and increasing the residence time in the reaction zone (comprising gas/liquid contact and circulating zones) that is necessary to attain the desired conversion of acrolein.

Preferably, the liquid holdup is sufficient to provide a conversion in the gas/liquid contact zone of at least about 95%, more preferably at least 99%, most preferably at least about 99.5%. For this purpose, the holdup is preferably sufficient to provide an effective residence time in the gas/liquid contact zone of about 2 to about 5 hours, more preferably about 3 to about 4 hours, based on net production of MMP. In a tray column of conventional design, a conversion of at least 99.5% can be realized with a liquid holdup providing an effective residence time of not greater than about 4 hours. This corresponds to acrolein and methyl mercaptan concentrations of not greater than about 0.5% by weight in the MMP product fraction. Because the reaction is mass transfer limited, no significant additional reaction volume need be provided in the circulation zone, for example, in the column sump or a circulating MMP pump tank. Thus, the ratio of the liquid holdup volume in the gas/liquid contact zone to the working volume of the circulation zone is advantageously at least about 2, preferably at least about 5, most preferably at least about 15 or even higher. As a practical matter, the residence time in the circulating zone is negligibly small, as compared to the gas/liquid contact zone in the column. For effective mass transfer and reaction heat removal, the rate of circulation through the column and heat exchanger(s) is generally at least several times the net rate of MMP production. Thus, it will be understood that the residence time per pass, based on the ratio of liquid holdup volume to circulation rate, need only be in the range of about 0.5 to about 1 hour, even though the effective residence time in the column based on the ratio of liquid holdup volume to net production rate is preferably in the ranges noted above.

A further advantage of operation in a countercurrent tray column is the attainment of a high rate of mass transfer at low gas pressure drop. It has been found that satisfactory mass transfer rates can be achieved with a pressure drop no greater than about 2 to about 5 psi.

In a further alternative, the system of FIG. 5 may be operated as a bubble column. However, the pressure drop in a bubble column is substantially greater than in either a tray or packed column. In those cases where relatively high pressure drop is acceptable, a gas lift reactor is preferred because of the turbulence created in the reactor upleg.

Figure 7:
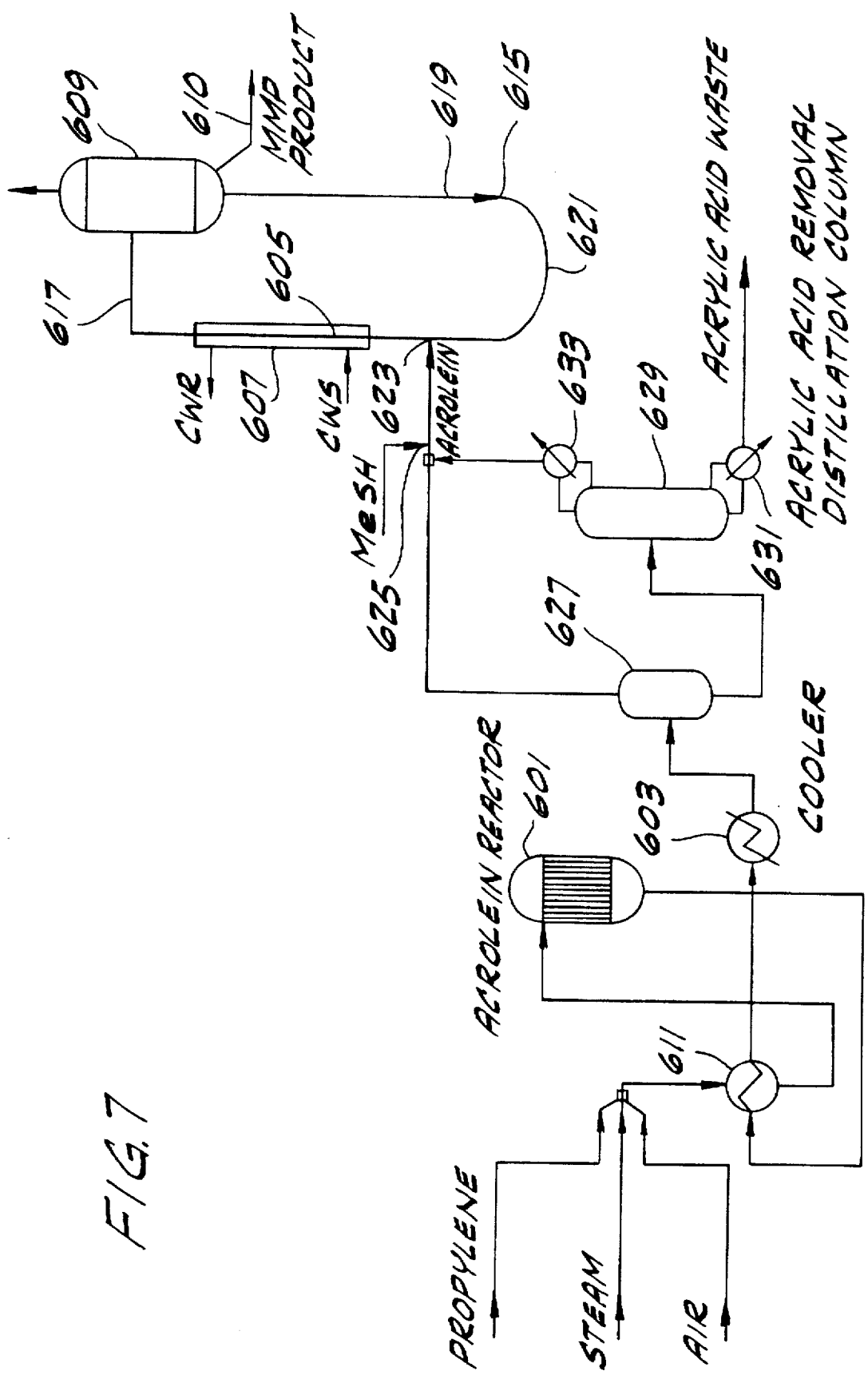
FIG. 7 is a schematic illustration of a process of the invention in which crude acrolein reaction product gas is treated for substantial removal of acrylic acid before the gas is introduced into a co-current gas lift reactor for reaction of acrolein with methyl mercaptan.
Figure 8:
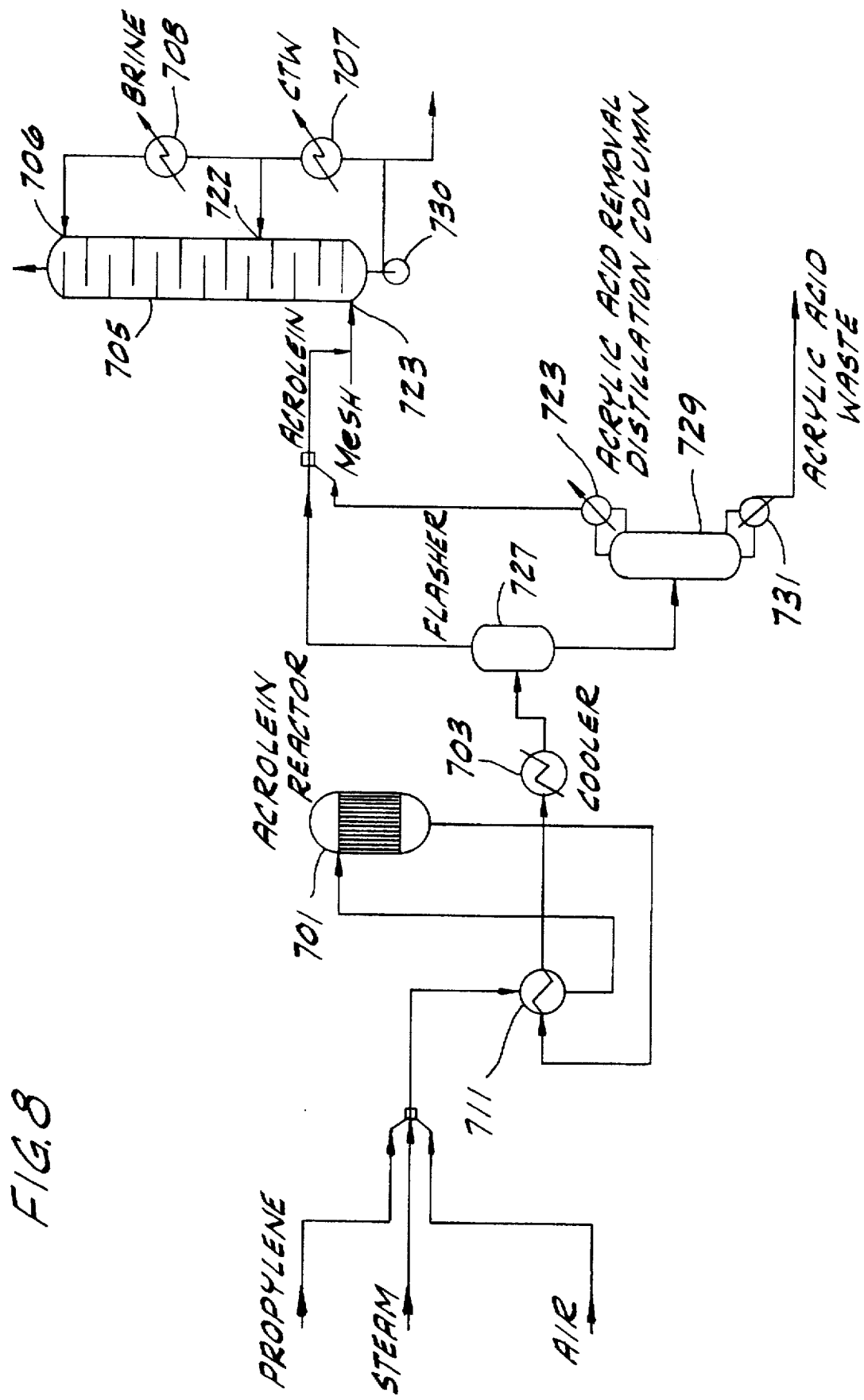
FIG. 8 is a schematic illustration of a process of the invention in which crude acrolein reaction product gas is treated for substantial removal of acrylic acid before the gas is introduced into a countercurrent tray column reactor for reaction of acrolein with methyl mercaptan.

Particularly preferred embodiments of the integrated process of the invention are illustrated in FIGS. 7 and 8. In each of these preferred processes, the crude acrolein reaction gas is treated to substantially eliminate acrylic acid from the gas, while assuring substantial recovery of essentially all acrolein. FIG. 7 illustrates the treatment process as applied in conjunction with a gas lift type MMP reaction system, while FIG. 8 illustrates the treatment process in conjunction with a low pressure countercurrent tray column MMP reactor.

In the process of FIG. 7, a mixture of propylene or other suitable hydrocarbon, steam, oxygen and non-condensables is passed over a suitable catalyst in an acrolein reactor 601 to produce a crude acrolein reaction gas having the composition described above. The feed mixture is preheated by transfer of heat from the crude reaction gas in a feed preheater comprising an indirect recuperative heat exchanger 611. The crude product is treated by further cooling it in an indirect heat exchanger 603, causing condensation of acrylic acid and water from the crude gas product. The gas phase exiting the cooler could be introduced directly into a continuous MMP reactor 605. However, the condensate formed in condenser 603 typically contains an amount of acrolein sufficient to justify recovery. Accordingly, in the process of FIG. 7, the condensate leaving the condenser is distilled to recover residual acrolein therefrom, producing a vapor phase that may be combined with the gas phase from the condenser to constitute feed to the reactor, and a liquid phase containing acrylic acid that is removed from the process. More particularly, as shown in the drawing, a two phase gas/liquid stream exits condenser 603 and flows to a flasher 627 where 35 it is further cooled, e.g., by transfer of heat to a cooling fluid in a coil inside the flasher. The flasher further serves as a vapor liquid separator, with condensate draining out the bottom thereof, and the gas phase flowing out the top. The condensate is directed to a fractionating column 629 provided with a reboiler comprising an indirect heat exchanger 631 and a condenser comprising an indirect heat exchanger 633. The column typically comprises at least 2, preferably 4 to 6, theoretical stages. Vapor exiting the top stage of the column is partially condensed in heat exchanger 633. The condensate is refluxed to the column and the vapor phase is mixed with the cooled acrolein gas phase leaving flasher 627. Preferably, the fraction of vapor condensed in heat exchanger 633 is such that the column operates at molar reflux ratio of at least about 0.5, preferably between about 1 and about 2. The bottoms stream from column 629 contains about 3% to about 5% acrylic acid in water, and has an acrolein content of less than 1% by weight, preferably not greater than about 0.1% by weight. Overheads from the column predominantly comprise acrolein, typically in a proportion greater than 75 mole %, more typically greater than about 90 mole %.

As illustrated in the drawing, overheads from column 629 are mixed with the gas phase exiting flasher 627 to provide the acrolein feed gas for reactor 605. The acrolein feed gas has the composition generally described above, but the acrylic acid content is consistently below 200 ppm, more typically below about 100 ppm. Reactor 605 operates in the same way as reactor 105 of FIG. 2, and jacket 607, upleg 617, downleg 619, bottom loop 621, acrolein feed point 623, and methyl mercaptan supply 625 all have the same function and essentially the same construction as the corresponding components of the reactor of FIG. 2.

The process of FIG. 8 utilizes an acrolein reactor 701, reaction gas/feed gas heat exchanger 711, a cooler and partial condenser 703 for removal of water and acrylic acid from the crude reaction gas, a flasher 727 and an acrylic acid fractionating column 729 which provide the same functions as reactor 601, heat exchanger 611, partial condenser 603, flasher 627 and acrylic acid column 629, respectively, of FIG. 7. Operation of the acrolein reaction and crude acrolein reaction gas treatment system of FIG. 8 is also comparable to that of FIG. 7, except that the preferred operating pressure in flasher 727 and fractionation column 729 of FIG. 8 is significantly lower than the preferred operating pressure in flasher 627 and column 629 of FIG. 7. For example, the preferred operating pressure in the acrylic acid removal circuit of FIG. 7 is between about 20 and about 30 psig, while the preferred operating pressure for the corresponding circuit of FIG. 8 is only about 15 to about 20 psig. Lower pressure drop across tray column 705 than across gas lift reactor 607 allows the lower pressure operation of the acrylic acid removal circuit of FIG. 8. Lower pressure operation allows even more efficient removal of acrylic acid, so that the treated acrolein feed gas entering reactor 705 typically contains <100 ppm, more typically <60 ppm acrylic acid. Again, overheads from column 729 contain at least about 75 mole %, more commonly at least about 90 mole % acrolein. Tray column reactor 705 operates in the same way as the reactor of FIG. 5, and methyl mercaptan and acrolein inlet 723, circulating pump 730, heat exchangers 707 and 708 and MMP liquid medium returns 706 and 722 have the same function, and essentially the same construction, as the corresponding components of the reaction system of FIG. 5.

Figure 6:
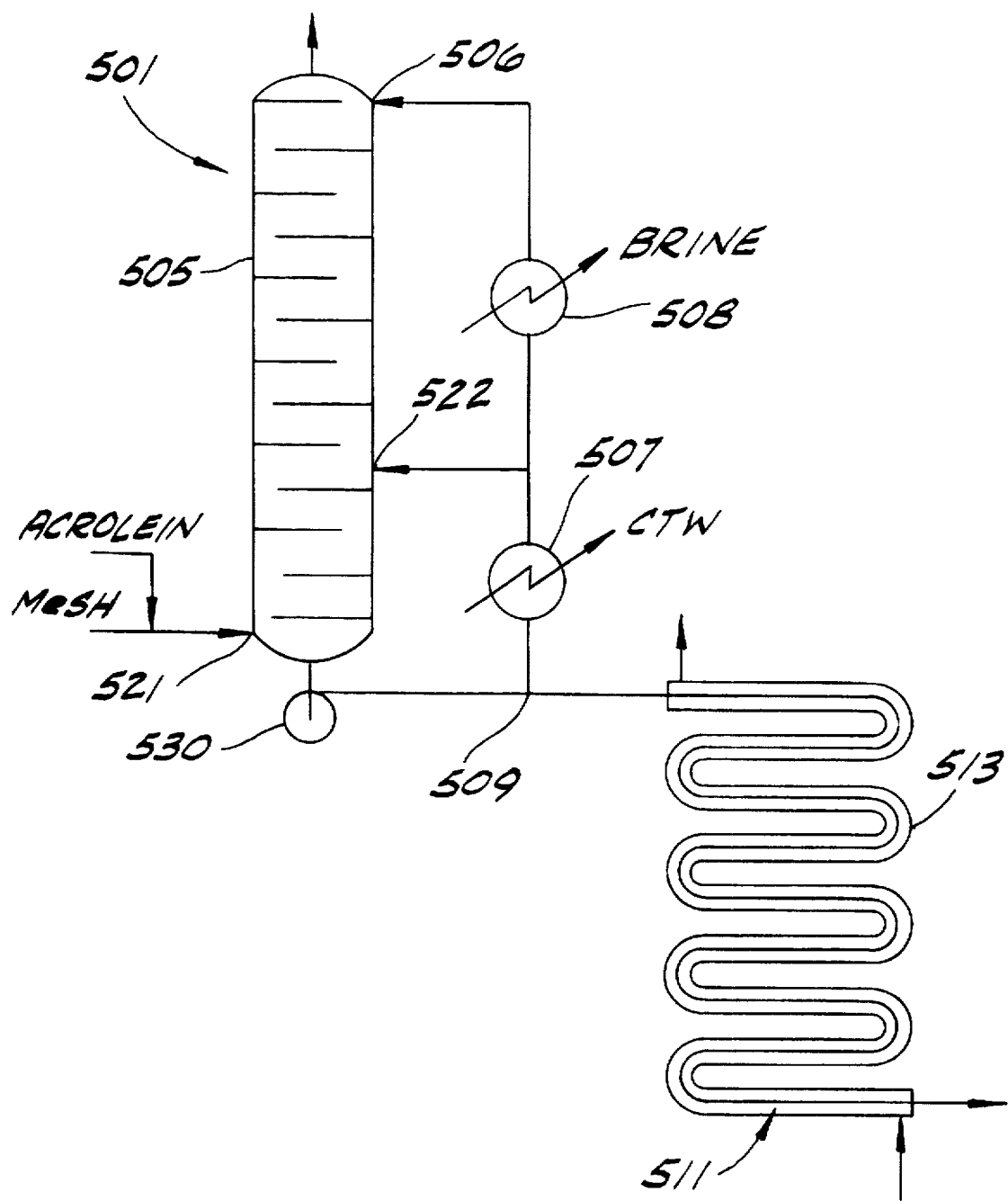
FIG. 6 is a schematic illustration of a process of the invention utilizing a tray column reactor followed by a plug flow reactor.

FIG. 6 illustrates a further alternative embodiment of the invention in which a partially or fully back mixed continuous reaction system 501 is designed or operated to provide a residence time less than that required for the ultimate conversion desired, and the reaction medium leaving reactor 501 is passed through a plug flow reactor 511 for completion of the reaction. Reactor 501 as illustrated in FIG. 6 comprises a tray column reactor. However, the use of a plug flow finishing reactor is equally applicable to either the circulating countercurrent gas/liquid flow reaction system of FIGS. 5 or 8, or the gas lift reactor of FIGS. 2 or 7. In the process of FIG. 6, acrolein and methyl mercaptan are fed through a gas inlet 521 at the bottom of a tray column reactor 505 of reaction system 501, and liquid MMP reaction medium is circulated through that system, entering at the top of the column through liquid inlet 506. Reaction heat is removed from the circulating MMP stream by transfer to cooling tower water in an indirect heat exchangers 507 and 508. A liquid reaction product fraction containing residual acrolein and methyl mercaptan is removed from the recirculating stream of system 501 through port 509 and thereafter passed through a plug flow reactor 511. Use of the plug flow reactor operated at a temperature in the range of between about 30° C. and about 70° C. with a residence time in the range of between about 0.1 and about 0.5 hours allows the residence time in the circulating countercurrent gas/liquid flow reaction system to be significantly lower than in the reaction system of FIG. 5. For example, where the residence time in the back mixed reaction system based on net outflow of product is only 0.2 to 1 hours (at a liquid holdup in a tray column reactor of 0.2 to 0.75 hour, e.g.), and the reaction product liquid fraction exiting this system through port 509 consequently contains between about 0.5% and about 1% each of acrolein and methyl mercaptan, a final reaction product containing not more than about 0.3% each of acrolein and methyl mercaptan may be produced at the exit of plug flow reactor 511 in a total residence time in the plug flow reactor of not more than about 0.5 hours. Plug flow reactor 511 operates substantially adiabatically. However, a jacket 513 provides for supply of heat or cooling as needed to maintain the temperature in the desired range.

MMP reaction product produced in the processes illustrated in FIGS. 1 to 8 may be used directly for the preparation of 4-(methylthio)butyronitrile without prior distillation for removal of either high boiling or low boiling impurities. This not only saves the capital and operating expense of providing distillation, but also avoids the yield losses inevitably resulting from the formation of additional high boilers in an MMP distillation column. 4-(Methylthio) butyronitrile (HMBN) may be produced by reaction of the MMP product with hydrogen cyanide. In turn, the HMBN can be converted to 2-hydroxy-4-methylthiobutanoic acid (HMBA) by hydrolysis with sulfuric or other mineral acid. Without distillation or other refining of either the MMP or the HMBN, the HMBN may be converted to HMBA which is suitable for use as an animal feed supplement serving as a source of methionine. MMP produced by the process of the invention may be converted to HMBN as described above, and the HMBN advantageously converted to HMBA by either the process described in Ruest et al. U.S. Pat. No. 4,524,077 or the process of Hernandez U.S. Pat. No. 4,912, 257. In the process of the Ruest patent, HMBN is hydrolyzed in sulfuric acid, the HMBA product extracted from the hydrolyzate using a substantially water-immiscible solvent, and the extract steam distilled to produce an 85 to 90% by weight aqueous solution of HMBA. In the process of the Hernandez patent, the hydrolyzate is neutralized with ammonia, causing it to separate into two phases, the organic phase being evaporated to produce an 85 to 90% aqueous solution of HMBA.

The following examples illustrate the invention.

EXAMPLE 1

MMP was prepared by reaction of methyl mercaptan and acrolein in a gas lift reactor of the type illustrated in FIG. 2. The height of the reactor was 3 feet (0.914 m) and the upleg had an inside diameter of 0.5 in. (1.27 cm.). Gas/liquid separator 109 comprised a cylinder having an overflow port for MMP product, a connection below the liquid surface for return of circulating MMP to the downleg of the reactor loop, and a vent at the top for release of non-condensable gases. Prior to the introduction of reactants, the reactor loop was filled with MMP containing about 0.4% by weight pyridinium acetate catalyst. Circulation of MMP in the reactor was commenced by sparging air through a 1/16" orifice at acrolein feed gas inlet 123. While air was sparged to induce circulation of the MMP, hot water was passed through jacket 107 to bring the circulating MMP to a controlled temperature of 41° F.

A synthetic crude acrolein stream was prepared having the composition set forth in Table 1. This stream was introduced into the reactor through the sparger at inlet 123. Methyl mercaptan vapor was introduced through the same orifice. Acrolein and methyl mercaptan were introduced through the sparger at a molar ratio of approximately 1.0 to 1.02. The absolute rates of introduction of the reactant streams is set forth in Table 1. Also set forth in Table 1 are the superficial gas velocity in the upleg, the reactor liquid volume, the residence time of liquid product in the reactor, the recovery of reactant feeds, the reactor yields, duration of the continuous run, average supplemental catalyst feed rate, and average rate of introduction of water in the acrolein feed gas.

The sparger at inlet 123 dispersed the two reactant feeds into the liquid in the upleg and created an aerated column for this leg. As a consequence, liquid in the non-aerated downleg was forced to flow downward into the bottom of the upleg through the bottom U bend, and continue to move upward through the dispersed gases in the upleg.

Within the two-phase upleg, from the gas sparger at the bottom to the separator at the top, a reactant mixture was formed which comprised a liquid phase containing MMP, methyl mercaptan and catalyst and a gas phase containing acrolein. The acrolein and methyl mercaptan were absorbed rapidly into the liquid phase and the two absorbed reactants reacted with each other to form MMP product. The rate of reaction was very rapid, but constituted the rate limiting step of the process. Some limited vapor phase reaction between the acrolein and the mercaptan also occurred. The temperature of the gas/liquid contact zone in the upleg of the reactor was maintained at about 41° F. by removing the exothermic heat of reaction to cooling water circulated through jacket 107.

Due to the highly turbulent and well dispersed two phase flow obtained by the simple gas lift system, without mechanical agitation or a recirculating pump, the single loop reactor achieved more than 95% recovery of the total reactant feeds (i.e., acrolein and methyl mercaptan) and virtually all the recovered reactants were converted into the desired MMP product in the same reactor loop. Composition of the product and the non-condensable vent gas stream are also set forth in Table 1.

Despite the higher than usual feed impurities (propylene, propane, acetaldehyde, propionaldehyde and water) contained in the acrolein feed gas stream, little or no by-product formation or product degradation was experienced as a result of the presence of these impurities. In particular, this and other experiments demonstrated that the reaction system is capable of tolerating a water impurity content of more than 3% by volume in the acrolein feed gas stream, and the resultant >6% by weight water content that is reached in the circulating liquid during operations at steady state.

As a result of the intense mixing provided by turbulent flow in the gas/liquid contact zone, and rapid circulation of MMP reaction medium, localized hot spots or concentration imbalances are avoided. This in turn inhibits formation of undesirable by-products.

TABLE 1

EXPERIMENTAL RESULTS AND MATERIAL BALANCES

| | |
|---|---|
| AVERAGE REACTOR TEMPERATURE | = 41.00 DEG C |
| MOLAR FEED RATIO, ACRO./MESH | = 0.99 |
| REACTOR LIQUID VOLUME | = 650.00 ML |
| RESIDENCE TIME OF LIQUID PRODUCT | = 4.97 HRS |
| RECOVERY OF REACTANT FEEDS | = 95.85% |
| REACTOR YIELDS: | |
| WT ALDEHYDE/WT <ACR + MESH> FEED | = 94.88% |
| MOL ALDEHYDE/MOL ACROL FEED | = 94.35% |
| MOL ALDEHYDE/MOL MESH FEED | = 94.35% |
| AVERAGE CATALYST FEED RATE | = 0.0102 G/MIN |

| | STREAM 1 <GAS MIX IN> | | STREAM 2 <MESH INLET> | | STREAM 3 <PRODUCT OUT> | | STREAM 4 <GAS OUTLET> | |
|---|---|---|---|---|---|---|---|---|
| | G/MIN | W% | G/MIN | W% | G/MIN | W% | G/MIN | W% |
| O2 | 0.675 | 14.934 | 0.0 | 0.0 | 0.0 | 0.0 | 0.675 | 20.571 |
| N2 | 2.222 | 49.158 | 0.0 | 0.0 | 0.0 | 0.0 | 2.222 | 67.713 |
| CO2 | 0.074 | 1.630 | 0.0 | 0.0 | 0.0 | 0.0 | 0.074 | 2.245 |
| CO | 0.016 | 0.360 | 0.0 | 0.0 | 0.0 | 0.0 | 0.016 | 0.495 |
| PROPYLENE | 0.062 | 1.372 | 0.0 | 0.0 | 0.0 | 0.0 | 0.062 | 1.889 |
| PROPANE | 0.063 | 1.394 | 0.0 | 0.0 | 0.0 | 0.0 | 0.063 | 1.920 |
| MESH | 0.0 | 0.0 | 1.018 | 100.0 | 0.010 | 0.438 | 0.025 | 0.608 |
| ACETALD | 0.024 | 0.539 | 0.0 | 0.0 | 0.004 | 0.195 | 0.020 | 0.608 |
| PROPALD | 0.081 | 1.792 | 0.0 | 0.0 | 0.022 | 0.992 | 0.059 | 1.783 |
| ACROLEIN | 1.174 | 25.979 | 0.0 | 0.0 | 0.012 | 0.507 | 0.017 | 0.531 |
| M-ALDEH | 0.0 | 0.0 | 0.0 | 0.0 | 2.080 | 91.733 | 0.049 | 1.480 |
| CATALYST | 0.0 | 0.0 | 0.0 | 0.0 | 0.011 | 0.465 | 0.0 | 0.0 |
| WATER | 0.129 | 2.844 | 0.0 | 0.0 | 0.129 | 5.669 | 0.0 | 0.0 |
| TOTAL | 4.520 | 100.00 | 1.018 | 100.00 | 2.267 | 100.00 | 3.281 | 100.00 |
| TEMP <C> | 51.0 | | 26.0 | | 40.0 | | 40.0 | |
| P <PSIG> | 8.4 | | 4.8 | | 0.0 | | 0.0 | |

EXAMPLE 2–23

Using the apparatus of FIG. 2, acrolein was reacted with methyl mercaptan to produce MMP. The process was carried out in the manner generally described in Example 1, but variations were made in operating temperature, molar ratio of acrolein to methyl mercaptan in the reactor feed, overall volumetric gas feed rate, and acrolein concentration in the gas feed mixture. These process conditions and the yields for the runs of examples 2–23 are set forth in Table 2.

Measurements or determinations were made of superficial gas velocity, inlet acrolein concentration, reaction temperature, catalyst concentration, residence time, and feed ratio of acrolein to methyl mercaptan. A statistical analysis was conducted to determine the effect of the latter operating variables on productivity, acrolein recovery, yield based on acrolein, acrolein concentration in the liquid phase, and methyl mercaptan concentration in the liquid phase. The results are set forth in Table 3.

TABLE 2

|  | Ex. 2 | Ex. 3 | Ex. 4 |
|---|---|---|---|
| AVERAGE OPERATING TEMP | 40.00 DEG C | 40.50 DEG C | 39.00 DEG C |
| MOLAR FEED RATIO, ACRO./MESH | 0.95 | 0.98 | 1.23 |
| GAS MIXTURE FLOW TO SPARGER, STP | 3.020 LITER/MIN | 2.826 LITER/MIN | 2.763 LITER/MIN |
| ACROLEIN CONC. IN GAS MIXTURE IN | 15.170 VOL % | 9.890 VOL % | 7.234 VOL % |
| ACROLEIN CONC. IN OUTLET GASES | 1.360 VOL % | 1.183 VOL % | 1.944 VOL % |
| SUPER. GAS VEL. IN UPLEG BOT., STP | 1.347 FT/SEC | 1.261 FT/SEC | 1.233 FT/SEC |
| REACTOR LIQUID VOLUME | 886.00 ML | 756.00 ML | 684.00 ML |
| RESIDENCE TIME OF LIQUID PROD. | 7.40 HRS | 11.54 HRS | 17.87 HRS |
| RECOVERY OF REACTANT FEEDS | 89.68% | 84.29% | 75.85% |
| REACTOR YIELDS: |  |  |  |
| WT ALDEHYDE/WT (ACR + MESH) FEED | 87.90% | 83.22% | 74.75% |
| MOL ALDEHYDE/MOL ACROL FEED | 89.97% | 84.13% | 68.40% |
| MOL ALDEHYDE/MOL MESH FEED | 85.59% | 82.17% | 83.81% |
| DURATION OF CONTINUOUS RUN | 5.10 HRS | 2.75 HRS | 2.75 HRS |
| AVERAGE CATALYST FEED RATE | 0.0105 G/MIN | 0.0061 G/MIN | 0.0061 G/MIN |
| AVERAGE WATER FEED RATE | 0.0 G/MIN | 0.0 G/MIN | 0.0 G/MIN |

|  | Ex. 5 | Ex. 6 | Ex. 7 |
|---|---|---|---|
| AVERAGE OPERATING TEMP | 41.00 DEG C | 40.00 DEG C | 40.00 DEG C |
| MOLAR FEED RATIO, ACRO./MESH | 1.07 | 1.26 | 1.17 |
| GAS MIXTURE FLOW TO SPARGER, STP | 3.128 LITER/MIN | 3.232 LITER/MIN | 3.249 LITER/MIN |
| ACROLEIN CONC. IN GAS MIXTURE IN | 16.563 VOL % | 20.648 VOL % | 9.240 VOL % |
| ACROLEIN CONC. IN OUTLET GASES | 2.560 VOL % | 4.467 VOL % | 2.417 VOL % |
| SUPER. GAS VEL. IN UPLEG BOT., STP | 1.395 FT/SEC | 1.441 FT/SEC | 1.449 FT/SEC |
| REACTOR LIQUID VOLUME | 741.00 ML | 738.00 ML | 760.00 ML |
| RESIDENCE TIME OF LIQUID PROD. | 6.08 HRS | 5.04 HRS | 12.85 HRS |
| RECOVERY OF REACTANT FEEDS | 87.44% | 88.12% | 76.32% |
| REACTOR YIELDS: |  |  |  |
| WT ALDEHYDE/WT (ACR + MESH) FEED | 85.47% | 85.53% | 75.32% |
| MOL ALDEHYDE/MOL ACROL FEED | 84.01% | 77.31% | 70.16% |
| MOL ALDEHYDE/MOL MESH FEED | 89.51% | 97.60% | 82.36% |
| DURATION OF CONTINUOUS RUN | 2.00 HRS | 1.58 HRS | 3.66 HRS |
| AVERAGE CATALYST FEED RATE | 0.0083 G/MIN | 0.0105 G/MIN | 0.0068 G/MIN |
| AVERAGE WATER FEED RATE | 0.0 G/MIN | 0.0 G/MIN | 0.0 G/MIN |

|  | Ex. 8 | Ex. 9 | Ex. 10 |
|---|---|---|---|
| AVERAGE OPERATING TEMP | 45.00 DEG C | 44.00 DEG C | 44.00 DEG C |
| MOLAR FEED RATIO, ACRO./MESH | 1.06 | 1.05 | 0.99 |
| GAS MIXTURE FLOW TO SPARGER, STP | 3.708 LITER/MIN | 2.538 LITER/MIN | 3.755 LITER/MIN |
| ACROLEIN CONC. IN GAS MIXTURE IN | 21.000 VOL % | 29.591 VOL % | 21.253 VOL % |
| ACROLEIN CONC. IN OUTLET GASES | 3.005 VOL % | 3.770 VOL % | 1.588 VOL % |
| SUPER. GAS VEL. IN UPLEG BOT., STP | 1.654 FT/SEC | 1.177 FT/SEC | 1.675 FT/SEC |
| REACTOR LIQUID VOLUME | 734.00 ML | 682.00 ML | 520.00 ML |
| RESIDENCE TIME OF LIQUID PROD. | 3.95 HRS | 3.50 HRS | 2.55 HRS |
| RECOVERY OF REACTANT FEEDS | 88.95% | 92.46% | 91.84% |
| REACTOR YIELDS: |  |  |  |
| WT ALDEHYDE/WT (ACR + MESH) FEED | 57.55% | 90.94% | 90.10% |
| MOL ALDEHYDE/MOL ACROL FEED | 85.33% | 88.82% | 90.40% |
| MOL ALDEHYDE/MOL MESH FEED | 90.26% | 93.52% | 89.73% |
| DURATION OF CONTINUOUS RUN | 3.20 HRS | 1.98 HRS | 2.40 HRS |
| AVERAGE CATALYST FEED RATE | 0.0182 G/MIN | 0.0252 G/MIN | 0.0139 G/MIN |
| AVERAGE WATER FEED RATE | 0.0 G/MIN | 0.0 G/MIN | 0.0 G/MIN |

|  | Ex. 11 | Ex. 12 | Ex. 13 |
|---|---|---|---|
| AVERAGE OPERATING TEMP | 50.00 DEG C | 42.00 DEG C | 43.00 DEG C |
| MOLAR FEED RATIO, ACRO./MESH | 1.00 | 1.04 | 0.96 |
| GAS MIXTURE FLOW TO SPARGER, STP | 3.760 LITER/MIN | 3.476 LITER/MIN | 3.619 LITER/MIN |
| ACROLEIN CONC. IN GAS MIXTURE IN | 19.405 VOL % | 14.409 VOL % | 18.471 VOL % |
| ACROLEIN CONC. IN OUTLET GASES | 2.100 VOL % | 2.138 VOL % | 1.285 VOL % |
| SUPER. GAS VEL. IN UPLEG BOT., STP | 1.677 FT/SEC | 1.550 FT/SEC | 1.703 FT/SEC |
| REACTOR LIQUID VOLUME | 527.00 ML | 529.00 ML | 649.00 ML |
| RESIDENCE TIME OF LIQUID PROD. | 2.89 HRS | 4.31 HRS | 3.51 HRS |
| RECOVERY OF REACTANT FEEDS | 89.52% | 87.37% | 92.64% |
| REACTOR YIELDS: |  |  |  |
| WT ALDEHYDE/WT (ACR + MESH) FEED | 88.01% | 85.57% | 90.52% |
| MOL ALDEHYDE/MOL ACROL FEED | 88.18% | 83.97% | 92.070% |

TABLE 2-continued

| | | | |
|---|---|---|---|
| MOL ALDEHYDE/MOL MESH FEED | 87.80% | 87.48% | 88.76% |
| DURATION OF CONTINUOUS RUN | 2.65 HRS | 2.48 HRS | 2.13 HRS |
| AVERAGE CATALYST FEED RATE | 0.0346 G/MIN | 0.0097 G/MIN | 0.0195 G/MIN |
| AVERAGE WATER FEED RATE | 0.0 G/MIN | 0.0571 G/MIN | 0.0 G/MIN |

| | Ex. 14 | Ex. 15 | Ex. 16 |
|---|---|---|---|
| AVERAGE OPERATING TEMP | 55.00 DEG C | 41.00 DEG C | 45.00 DEG C |
| MOLAR FEED RATIO, ACRO./MESH | 1.01 | 0.97 | 1.01 |
| GAS MIXTURE FLOW TO SPARGER, STP | 3.946 LITER/MIN | 2.924 LITER/MIN | 3.124 LITER/MIN |
| ACROLEIN CONC. IN GAS MIXTURE IN | 18.137 VOL % | 16.049 VOL % | 18.547 VOL % |
| ACROLEIN CONC. IN OUTLET GASES | 2.322 VOL % | 0.503 VOL % | 2.429 VOL % |
| SUPER. GAS VEL. IN UPLEG BOT., STP | 1.760 FT/SEC | 1.304 FT/SEC | 1.393 FT/SEC |
| REACTOR LIQUID VOLUME | 525.00 ML | 650.00 ML | 600.00 ML |
| RESIDENCE TIME OF LIQUID PROD. | 3.07 HRS | 4.97 HRS | 4.13 HRS |
| RECOVERY OF REACTANT FEEDS | 85.35% | 94.22% | 86.24% |
| REACTOR YIELDS: | | | |
| WT ALDEHYDE/WT (ACR + MESH) FEED | 83.94% | 92.34% | 84.06% |
| MOL ALDEHYDE/MOL ACROL FEED | 83.58% | 93.79% | 83.84% |
| MOL ALDEHYDE/MOL MESH FEED | 84.36% | 90.68% | 84.31% |
| DURATION OF CONTINUOUS RUN | 2.27 HRS | 4.88 HRS | 4.42 HRS |
| AVERAGE CATALYST FEED RATE | 0.0162 G/MIN | 0.0102 G/MIN | 0.0113 G/MIN |
| AVERAGE WATER FEED RATE | 0.0 G/MIN | 0.0922 G/MIN | 0.1018 G/MIN |

| | Ex. 17 | Ex. 18 | Ex. 19 |
|---|---|---|---|
| AVERAGE OPERATING TEMP | 42.00 DEG C | 40.00 DEG C | 39.00 DEG C |
| MOLAR FEED RATIO, ACRO./MESH | 0.95 | 1.06 | 1.13 |
| GAS MIXTURE FLOW TO SPARGER, STP | 3.238 LITER/MIN | 2.481 LITER/MIN | 2.073 LITER/MIN |
| ACROLEIN CONC. IN GAS MIXTURE IN | 15.622 VOL % | 25.019 VOL % | 29.440 VOL % |
| ACROLEIN CONC. IN OUTLET GASES | 0.961 VOL % | 3.160 VOL % | 2.772 VOL % |
| SUPER. GAS VEL. IN UPLEG BOT., STP | 1.444 FT/SEC | 1.160 FT/SEC | 0.925 FT/SEC |
| REACTOR LIQUID VOLUME | 880.00 ML | 800.00 ML | 800.00 ML |
| RESIDENCE TIME OF LIQUID PROD. | 6.60 HRS | 5.48 HRS | 5.14 HRS |
| RECOVERY OF REACTANT FEEDS | 92.06% | 86.71% | 96.40% |
| REACTOR YIELDS: | | | |
| WT ALDEHYDE/WT (ACR + MESH) FEED | 89.09% | 82.06% | 93.72% |
| MOL ALDEHYDE/MOL ACROL FEED | 91.38% | 79.94% | 88.76% |
| MOL ALDEHYDE/MOL MESH FEED | 86.53% | 84.65% | 100.23% |
| DURATION OF CONTINUOUS RUN | 5.33 HRS | 5.40 HRS | 4.00 HRS |
| AVERAGE CATALYST FEED RATE | 0.0134 G/MIN | 0.0157 G/MIN | 0.0167 G/MIN |
| AVERAGE WATER FEED RATE | 0.0 G/MIN | 0.0 G/MIN | 0.0 G/MIN |

| | Ex. 20 | Ex. 21 | Ex. 22 |
|---|---|---|---|
| AVERAGE OPERATING TEMP | 37.00 DEG C | 43.00 DEG C | 46.00 DEG C |
| MOLAR FEED RATIO, ACRO./MESH | 0.94 | 0.70 | 1.25 |
| GAS MIXTURE FLOW TO SPARGER, STP | 2.259 LITER/MIN | 2.440 LITER/MIN | 2.531 LITER/MIN |
| ACROLEIN CONC. IN GAS MIXTURE IN | 26.870 VOL % | 27.026 VOL % | 33.558 VOL % |
| ACROLEIN CONC. IN OUTLET GASES | 1.850 VOL % | −2.753 VOL % | 12.143 VOL % |
| SUPER. GAS VEL. IN UPLEG BOT., STP | 1.008 FT/SEC | 1.088 FT/SEC | 1.129 FT/SEC |
| REACTOR LIQUID VOLUME | 850.00 ML | 765.00 ML | 792.00 ML |
| RESIDENCE TIME OF LIQUID PROD. | 5.25 HRS | 3.83 HRS | 4.95 HRS |
| RECOVERY OF REACTANT FEEDS | 92.91% | 92.23% | 74.65% |
| REACTOR YIELDS: | | | |
| WT ALDEHYDE/WT (ACR + MESH) FEED | 90.42% | 88.57% | 71.13% |
| MOL ALDEHYDE/MOL ACROL FEED | 93.31% | 105.97% | 64.65% |
| MOL ALDEHYDE/MOL MESH FEED | 87.25% | 74.33% | 80.53% |
| DURATION OF CONTINUOUS RUN | 3.00 HRS | 2.40 HRS | 1.40 HRS |
| AVERAGE CATALYST FEED RATE | 0.0139 G/MIN | 0.0069 G/MIN | 0.0 G/MIN |
| AVERAGE WATER FEED RATE | 0.0 G/MIN | 0.0 G/MIN | 0.0 G/MIN |

| | Ex. 23 |
|---|---|
| AVERAGE OPERATING TEMP | 39.00 DEG C |
| MOLAR FEED RATIO, ACRO./MESH | 0.63 |
| GAS MIXTURE FLOW TO SPARGER, STP | 2.276 LITER/MIN |
| ACROLEIN CONC. IN GAS MIXTURE IN | 19.476 VOL % |
| ACROLEIN CONC. IN OUTLET GASES | −1.573 VOL % |
| SUPER. GAS VEL. IN UPLEG BOT., STP | 1.015 FT/SEC |
| REACTOR LIQUID VOLUME | 792.00 ML |
| RESIDENCE TIME OF LIQUID PROD. | 5.65 HRS |
| RECOVERY OF REACTANT FEEDS | 91.16% |
| REACTOR YIELDS: | |
| WT ALDEHYDE/WT (ACR + MESH) FEED | 82.88% |

TABLE 2-continued

| | |
|---|---|
| MOL ALDEHYDE/MOL ACROL FEED | 105.03% |
| MOL ALDEHYDE/MOL MESH FEED | 66.51% |
| DURATION OF CONTINUOUS RUN | 5.00 HRS |
| AVERAGE CATALYST FEED RATE | 0.0 G/MIN |
| AVERAGE WATER FEED RATE | 0.0 G/MIN |

TABLE 3

EXPERIMENTAL RESULTS ON THE EFFECTS OF OPERATING VARIABLES

| | VARIABLES | | | | | | RESULTS | | | | |
|---|---|---|---|---|---|---|---|---|---|---|---|
| RUN NO. | VG (F/S) | YA (M%) | T (C) | CC (W%) | TR (HR) | A/M (RATIO) | PR (G/M) | REC (%) | YIELD (%) | CA (W%) | CM (W%) |
| 041684 (TYPICAL) | 1.30 | 16.1 | 41 | .47 | 5.0 | 0.97 | 2.27 | 94.2 | 92.3 | 0.51 | 1.34 |
| 010984A | 1.02 | 19.5 | 39 | 0.4 | 5.7 | 0.63 | 2.34 | 91.2 | 82.9 | .051 | 8.85 |
| 011984B | 1.13 | 33.6 | 46 | 0.4 | 5.0 | 1.25 | 2.77 | 74.7 | 71.1 | 4.35 | 0.20 |
| 042584 | 1.76 | 18.1 | 55 | 0.4 | 3.1 | 1.01 | 2.94 | 85.4 | 83.9 | 1.30 | 0.28 |
| 050284 | 1.68 | 19.4 | 50 | 0.7 | 2.9 | 1.00 | 3.13 | 89.5 | 88.0 | 0.05 | 1.60 |
| 061384B | 1.44 | 20.7 | 40 | .39 | 5.0 | 1.26 | 2.54 | 88.1 | 85.5 | 2.43 | 0.43 |
| 061384A | 1.40 | 16.6 | 41 | .32 | 6.1 | 1.07 | 2.11 | 87.4 | 86.5 | .158 | .913 |
| 052384 | 1.45 | 9.24 | 40 | .43 | 12.8 | 1.17 | 1.03 | 76.3 | 75.3 | .775 | .487 |
| 061484B | 1.23 | 7.23 | 39 | .39 | 17.9 | 1.23 | 0.66 | 75.9 | 74.8 | 1.12 | .291 |

VG = SUPERFICIAL GAS VELOCITY, FT/SEC
YA = INLET ACROLEIN CONC., MOLE %
T = REACTOR TEMPERATURE, DEG. C
CC = CATALYST (PYRIDINE ACETATE) CONC., WT. %
TR = RESIDENCE TIME BASED ON PRODUCT RATE, HOUR
A/M = FEED RATIO OF ACROLEIN TO MESH, MOLE RATIO
PR = THE RATE OF PRODUCT MADE, G/MIN
REC = PERCENT ACROLEIN RECOVERED FROM FEED, %
YIELD = PERCENT FEED ACROLEIN CONVERTED TO ALDEHYDE PRODUCT, %
CA = ACROLEIN CONC. IN LIQUID, WT. %
CM = MESH CONC. IN LIQUID, WT. %

EXAMPLE 24

Using a process of the type illustrated in FIG. 2, a 50 hour continuous run was conducted with an acrolein feed gas produced by catalytic oxidation of propylene in a laboratory reactor. During the run, the temperature of the gas lift loop was controlled at about 40° C. and the acrolein to methyl mercaptan feed ratio was constantly monitored by means of a discrete gas chromatography analysis of a reactor liquid sample every half hour. The final aldehyde product had the following composition:

| | |
|---|---|
| Acetaldehyde | 0.11 wt. % |
| Methyl Mercaptan | 0.88 |
| Acrolein | 0.07 |
| Allyl Alcohol | 0.29 |
| Acetic Acid | 0.35 |
| Acrylic Acid | 0.52 |
| β-hydroxypropionaldehyde | 0.27 |
| Pyridine | 0.19 |
| MMP | 89.02 |
| By-product having MW = 190 | 0.19 |
| Water | 7.00 |

In a commercial operation in which water is controlled to a more typical level, e.g., 2%, the MMP assay would be greater than 94% The relatively high proportion of β-hydroxypropionaldehyde was a result of the presence of water at well above the level readily achievable by cooling the acrolein feed gas in a commercial process.

EXAMPLE 25

Using a process of the type illustrated in FIG. 2, comparative tests were conducted on a wetted wall reactor and a horizontal loop reactor. A synthetic acrolein feed gas was used in these runs. During steady state operation, liquid product samples were analyzed by gas chromatography to determine aldehyde assay, residual acrolein, methyl mercaptan and by-product impurities. Based on these analyses, calculations were made to determine the percent acrolein recovery, product yield and reactor material balance for each run. Average mass transfer coefficient and reaction kinetic rate constants were obtained by fitting experimental data to a two-phase reactor model. Gas holdup and liquid recirculation rate data were also measured and correlated.

Physical dimensions of the reactor systems are set forth in Table 4, together with the temperature, gas rate and liquid rate for each run. A comparison of reaction conditions, feed rates, yields, and average mass transfer coefficients is set forth in Table 5.

TABLE 4

REACTOR SIZES AND OPERATING VARIABLES

| REACTOR | TUBE SIZE | SEPARATOR | TEMP. | GAS RATE | LIQUID RATE |
|---|---|---|---|---|---|
| Gas-lift | .5" id × 3.5' (or 5' w/ spool) | 2.5" od × 8" | 35–55 C | 2.2–4.0 l/m | 4.0–12 l/m |
| Wetted Wall | .5" id × 4.5' | 4" od × 6" | 30–48 C | 3.0–6.5 l/m | .6–.8 l/m |
| Horiz. Loop | .5" id × 7.5' | 3" od × 11" 4" od × 13" | 37–40 C | 2.5–3.4 l/m | 9.5–13.3 l/m |

TABLE 5

TYPICAL RESULTS OF REACTOR TESTED

| | GAS LIFT | WETTED WALL | HORIZ. LOOP |
|---|---|---|---|
| Run No. | 041684 | 110184 | 011685 |
| Inlet Gasa Conc. Vol % acrol. | 16.0 | 16.8 | 17.3 |
| Outlet Gas Conc. Vol % acrol. | 0.503 | 1.92 | 3.82 |
| Reactor Temp., C | 41.0 | 36.0 | 40.0 |
| Superficial Vel. Gas, f/s | 1.304 | 1.46 | 1.39 |
| Liq., f/s | 3.5 | 0.3 | 5.7 |
| Liquid Conc. Wt. % acrol. | 0.51 | 0.71 | 0.05 |
| Wt. % MeSH | 1.30 | 0.20 | 1.35 |
| Gas Mixture Feed Rate, g/m | 4.43 | 4.84 | 4.56 |
| Acrol. Feed Rate, g/m | 1.174 | 1.372 | 1.352 |
| MeSH Vap. Feed Rate, g/m | 1.042 | 1.160 | 1.095 |
| Aldehyde Product Rate, g/m | 2.267 | 2.306 | 2.118 |
| Feed Recovery (acrol. + MeSH), wt. % | 94.2 | 88.2 | 82.1 |
| Reactor Yield (ald./ acr + MeSH, wt. % | 92.34 | 87.33 | 80.97 |
| Ave. Mass Transfer Coeff., mol/l-atm-h | 150 | 120 | 50 |

EXAMPLE 26

In accordance with the process illustrated in FIG. 5, a reaction medium comprising MMP and methyl mercaptan and catalyst is contacted with an acrolein vapor stream in a tray column containing 20 trays. None of the MMP reaction medium exiting cooler 407 is recycled to the bottom portion of the tower. Instead, all of the circulating MMP is passed through cooler 408 and recycled to the top of the column. Stage cooling is provided by indirect heat transfer from the liquid phase at the bottom stage and at the 5th stage from the bottom. The acrolein vapor stream is introduced into the bottom of the column at a rate of 662.4 lb. moles per hour, and contains 15% by volume acrolein, 0.28% by volume acetaldehyde, 17% by volume water vapor, and 83% by volume non-condensables. Methyl mercaptan is introduced into the bottom of the column at a rate of 100 lb. moles/hr.

MMP reaction medium is introduced into the top of the column at a rate of about 600 lb. moles/hr. An MMP product stream containing 97.3% by weight MMP is removed from the process in the column at a rate of about 110.4 lb. moles/hr.

EXAMPLE 27

MMP (428.1 grams) produced in Example 24 was charged to a 1,000 ml reactor provided with cooling jacket and agitator. HCN (105.4 grams) was metered into the same reactor over a period of 50 minutes, during which temperature was maintained at between 35° and 40° C. At the end of the HCN feed, temperature was raised to 45° C. and the reaction was allowed to continue for an additional 30 minutes to complete the conversion of MMP to 2-hydroxy-4-methylthiobutyric acid (HMBN) (527.7 grams) which was analyzed and found to contain 90.8% HMBN with the remainder mostly water, catalyst and some low level impurities.

EXAMPLE 28

HMBN (515 grams) prepared from Example 27 was added to 65.9% by weight aqueous sulfuric acid solution (584.2 grams) at 60° C. over a period of 50-minutes in a 1,000 ml jacketed reactor provided with agitator. The resulting mixture was allowed to react for an additional 10 minutes at 65° C. to complete the first hydrolysis reaction which converts HMBN to the corresponding amide. Then, hot water (378.5 grams) at 80° C. was added to the mixture in the reactor and the temperature of the mixture was raised to 8° C. to effect the second hydrolysis reaction that converts amide to HMEA and by-product ammonium bisulfate. The reaction was allowed to continue for two and one half hours to finish the second hydrolysis. Alternatively, the required reaction time may be reduced by approximately 50% by increasing the hydrolysis temperature to 90°–100° C. range. The final hydrolyzate was analyzed and found to contain 32.1% HMBA monomer, 0.11% HMBA dimer, and less than 0.02% each of amide and nitrile, with the remainder being ammonium bisulfate by-product and water. The above hydrolyzate was contacted with methyl isobutyl ketone (MIBK) solvent to extract HMBA product. The extract was evaporated to separate the solvent from HMBA under vacuum at 70° C. The bottom solvent-free product was analyzed and found to contain 74.8% HMBA monomer and 7.0% HMBA dimer, the remainder being mostly water and sulfate ion. This product contains a slightly higher than normal water content. The water content may be reduced to the normal 11–12% range by further evaporation.

EXAMPLE 29

In accordance with the process illustrated in FIG. 7, propylene is catalytically oxidized to produce a crude acrolein reaction product gas in catalytic reactor 601. A mixture of propylene, steam and air is fed to the reactor through heat exchanger 611 where it is preheated by transfer of heat from the reaction product gas. Reaction product gas is cooled and partially condensed in heat exchanger 603 to produce a mixed liquid/vapor stream at a temperature of 37.8° C. This stream is then introduced into flasher 627 where it is further cooled and separated into a cooled gas stream containing acrolein (18.9% by weight), nitrogen (71.1% by weight), oxygen (2.8% by weight), propane (2.1% by weight), propylene (1.8% by weight), water vapor (0.96% by weight), acrylic acid (80 ppm), acetaldehyde (0.20% by weight), carbon monoxide (0.6% by weight), carbon dioxide (1.7% by weight), and formalin (140 ppm), and a condensate stream containing water (75.4% by weight), acrolein (20.0% by weight), and acrylic acid (3.1% by weight). Both the cooled gas stream and the condensate are at a temperature of 23.2° C. and an absolute pressure of 26 psi. The condensate is introduced into fractionating column 629 where it is distilled at a head pressure of 23 psi. Vapor exiting the top stage of the column is partially condensed, and the condensate refluxed to the column at a molar reflux ratio of 1. An aqueous waste product is produced at the bottom of the column which contains acrylic acid (3.9% by weight) and acrolein (711 ppm). The overhead product contains acrolein (94.2% by weight), acetaldehyde (1.1 by weight), water vapor (4.6% by weight), and less than 1 ppm acrylic acid. The overheads from the fractionating column are mixed with the cooled gas stream exiting the flasher to produce a combined acrolein gas stream containing acrolein (24.6% by weight), acetaldehyde (0.3% by weight), water vapor (1.2% by weight), propane (1.9% by weight), propylene (1.6% by weight), and acrylic acid (76 ppm) at a temperature of 26.5° C. and a total pressure of 23 psia. This gas is introduced together with methyl mercaptan via inlet 623 into circulating MMP reaction medium in the lower return loop 621 of gas lift reactor 605. Acrolein absorption and reaction occur in flow through the upleg yielding a product which exits the upleg at the temperature of 40° C. and a pressure of 16 psia containing MMP (75.9% by weight), methyl mercaptan (0.2% by weight), acrolein (0.3% by weight), water (1.5% by weight), propane (0.5% by weight), propylene (0.5% by weight), nitrogen (19.1% by weight), oxygen (0.8% by weight), acetaldehyde (0.1% by weight), formalin (157 ppm), acrylic acid (126 ppm), pyridine (0.2% by weight), and acetic acid (0.2% by weight). Non-condensables are separated from liquid MMP reaction medium in gas/liquid separator 609 and the MMP reaction medium is recirculated through the downleg and the bottom loop for return to the upleg of the reactor and mixing with further acrolein gas and methyl mercaptan. MMP product is removed at a temperature of 40° C. and 15 psi and contains MMP (97.4% by weight), acetic acid (0.2% by weight), pyridine (0.2% by weight), methyl mercaptan (80 ppm), formalin (180 ppm), acetaldehyde (520 ppm), acrylic acid (160 ppm), water (1.8% by weight), and acrolein (0.2% by weight).

EXAMPLE 30

In accordance with the process illustrated in FIG. 8, propylene is catalytically oxidized to produce a crude acrolein reaction product gas in catalytic reactor 701. A mixture of propylene, steam and air is fed to the reactor through heat exchanger 711 where it is preheated by transfer of heat from the reaction product gas. Reaction product gas is cooled and partially condensed in heat exchanger 703 to produce a mixed liquid vapor stream at a temperature of 37.8° C. This stream is then introduced into flasher 727 where it is further cooled and separated into a cooled gas stream containing acrolein (19.1% by weight), nitrogen (71.0% by weight), oxygen (2.8% by weight), propylene (1.8% by weight), propane (2.1% by weight), water vapor (0.9% by weight), acrylic acid (40 ppm), acetaldehyde (0.2% by weight), carbon monoxide (0.6% by weight), carbon dioxide (1.7% by weight), and formalin (140 ppm), and a condensate stream containing water (75.8% by weight), acrolein (19.5% by weight), acetaldehyde (0.5% by weight) and acrylic acid (3.1% by weight). Both the cooled gas stream and the condensate are at a temperature of 15.2° C. and an absolute pressure of 17 psi. The condensate is introduced into fractionating column 729 where it is distilled at a head pressure of 15 psi. Vapor leaving the top stage of the column is partially condensed and the condensate refluxed to the column at a molar reflux ratio of 1. An aqueous waste product is produced at the bottom of the column which contains acrylic acid (3.9% by weight) and acrolein (0.6% by weight). The overhead product contains acrolein (94.0% by weight), acetaldehyde (0.2% by weight), water vapor (3.6% by weight), and less than 1 ppm acrylic acid. The overheads from the fractionating column are mixed with the cooled gas stream exiting the flasher to produce a combined acrolein gas stream containing acrolein (24.5% by weight), acetaldehyde (0.3% by weight), water vapor (1.0% by weight), propane (1.9% by weight), propylene (1.6% by weight), and acrylic acid (76 ppm) at a temperature of 18.2° C. and a total pressure of 16 psia. This gas is introduced together with methyl mercaptan into circulating MMP via inlet 723 at the bottom of tray column reactor 705. Gas flows upwardly through the column countercurrently to downwardly flowing MMP reaction medium. Reaction medium comprising MMP (96.7% by weight), acrolein (962 ppm), and methyl mercaptan (0.14% by weight) enters the top of the column at a temperature of 0° C. Reaction product exiting the column at a temperature of 62° C. contains methyl mercaptan (0.14% by weight), acrolein (960 ppm), and MMP (96.8% by weight). The reaction product is circulated through heat exchanger 707 where it is cooled to 32.2° C. by indirect heat transfer to cooling water. Slightly less than two-thirds of the circulating stream is recycled from the exit of heat exchanger 707 to a tray at about the mid-point of reactor 705. The remaining portion of the circulating reaction medium is mixed with catalyst and passed through heat exchanger 708 where it is cooled to a temperature of 0° C. by indirect heat transfer to refrigerated brine. The portion of the recirculating medium exiting heat exchanger 708 is recycled via line 706 to the top of tray column reactor 705. A product stream is removed from the circulating MMP reaction medium at a point between the bottom of tray column reactor 705 and the inlet to heat exchanger 707. Alternatively, the product may be recovered from the outlet of either cooler 707 or cooler 708. The product stream contains MMP (96.8% by weight), methyl mercaptan (0.14% by weight), and acrolein (960 ppm). The ratio between the rate of MMP reaction medium recirculation and the rate of net product withdrawal is about 15 to 1.

What is claimed is:

1. A process for the continuous preparation of 3-(methylthio)propanal, comprising:

contacting a gaseous acrolein feed stream with a liquid reaction medium in a gas/liquid contact zone, said reaction medium containing 3-(methylthio)propanal and a catalyst for the reaction between methyl mercaptan and acrolein, said gaseous acrolein feed stream comprising acrolein vapor and non-condensable gas, whereby acrolein from said feed stream is transferred to said liquid medium;

introducing methyl mercaptan into said reaction medium in a proportion which is substantially stoichiometrically equivalent to the acrolein introduced into said medium, and reacting acrolein and methyl mercaptan in said liquid medium without substantial formation of the intermediate hemi(methylthio)acetal of 3-(methylthio)

propanal to produce a liquid reaction product containing 3-(methylthio)propanal;

dividing said reaction product into a product fraction and a circulating fraction; and recycling said circulating fraction to said gas/liquid contact zone.

2. A process as set forth in claim 1 wherein acrolein and methyl mercaptan are reacted in said liquid medium in a reaction zone that comprises a circulation zone into which said liquid reaction product is discharged from said gas/liquid contact zone and through which said circulating fraction is circulated back to said gas/liquid contact zone, methyl mercaptan being introduced into said reaction zone at a location or locations such that no excess of methyl mercaptan prevails in any region of said reaction zone for a time long enough for substantial formation of said intermediate hemi(methylthio)acetal.

3. A process for the continuous preparation of 3-(methylthio)propanal, comprising:

contacting a liquid reaction medium with a gaseous acrolein feed stream in a gas/liquid contact zone through which said feed stream and said reaction medium are passed countercurrently, said reaction medium containing 3-(methylthio)propanal and a catalyst for the reaction between methyl mercaptan and acrolein, said gaseous acrolein feed stream comprising acrolein vapor and non-condensable gas, whereby acrolein is transferred from said feed stream to said reaction medium;

reacting acrolein with methyl mercaptan in said medium to produce a liquid reaction product containing 3-(methylthio)propanal, the liquid holdup in said countercurrent gas/liquid contact zone being sufficient to effect conversion in said gas/liquid contact zone of at least 90% of the acrolein contained in said feed gas;

separating said non-condensable gas from said liquid reaction product;

dividing said reaction product into a product fraction and a circulating fraction; and recycling said circulating fraction to said gas/liquid contact zone.

4. A process for the continuous preparation of 3-(methylthio)propanal, comprising:

contacting a liquid reaction medium with a gaseous acrolein feed stream in a gas/liquid contact zone, said reaction medium containing 3-(methylthio)propanal and a catalyst for the reaction between methyl mercaptan and acrolein, said gaseous acrolein feed stream comprising acrolein vapor and non-condensable gas, whereby acrolein is transferred from said feed stream to said reaction medium;

reacting acrolein and methyl mercaptan in said liquid reaction medium to produce an intermediate liquid reaction product; separating said non-condensable gas from said intermediate liquid reaction product;

dividing said intermediate liquid reaction product into an intermediate product fraction and a circulating fraction; and recycling said circulating fraction to said gas/liquid contact zone; and passing said intermediate product fraction through a plug flow reactor to convert residual acrolein and methyl mercaptan to 3-(methylthio)propanal.

5. A process for the continuous preparation of 3-(methylthio)propanal, comprising:

cooling a crude reaction product gas stream obtained from the catalytic oxidation of a hydrocarbon, thereby producing a cooled gas stream comprising acrolein and a condensate comprising water, acrylic acid and a residual proportion of acrolein;

separating said condensate from said cooled gas stream; fractionally distilling said condensate to produce an overhead fraction comprising acrolein and a bottoms fraction which is substantially free of acrolein;

mixing said overhead fraction with said cooled gas stream to produce a combined acrolein gas stream;

contacting a liquid reaction medium with a gaseous acrolein feed stream in a gas/liquid contact zone, said reaction medium containing 3-(methylthio)propanal and a catalyst for the reaction between methyl mercaptan and acrolein, said gaseous acrolein feed stream comprising said combined acrolein gas stream and containing acrolein vapor, non-condensable gas and water vapor, whereby acrolein is transferred from said feed stream to said reaction medium;

reacting acrolein with methyl mercaptan in said medium to produce a liquid reaction product containing 3-(methylthio)propanal;

dividing said reaction product into a product fraction and a circulating fraction; and recycling said circulating fraction to said gas/liquid contact zone.

6. A process for the continuous preparation of 3-(methylthio)propanal, comprising:

contacting a gaseous acrolein feed stream with a liquid reaction medium, said reaction medium containing 3-(methylthio)propanal and a catalyst for the reaction between methyl mercaptan and acrolein, said gaseous acrolein feed stream comprising acrolein vapor and non-condensable gas, whereby acrolein from said feed stream is transferred to said liquid medium;

introducing methyl mercaptan into said reaction medium in a proportion which is substantially stoichiometrically equivalent to the acrolein introduced into said medium, and reacting acrolein and methyl mercaptan in said liquid medium in a first reaction zone without substantial formation of the intermediate hemi(methylthio)acetal of 3-(methylthio)propanal to produce a liquid reaction product containing 3-(methylthio)propanal and residual acrolein; and passing the reaction product from said first reaction zone through a second reaction zone comprising a plug flow reactor to convert residual acrolein and methyl mercaptan to 3-(methylthio)propanal.

* * * * *